United States Patent
Gebert et al.

(10) Patent No.: US 12,057,244 B2
(45) Date of Patent: Aug. 6, 2024

(54) PROCESS FOR PREPARING A PROCESSED FILAMENT, INCLUDING INTERACTION OF A SEGMENT WITH AT LEAST ONE BEAM OF ELECTROMAGNETIC RADIATION OF A FIRST KIND

(71) Applicants: Heraeus Deutschland GmbH & Co. KG, Hanau (DE); Heraeus Medical Components LLC, St. Paul, MN (US)

(72) Inventors: Jörg-Martin Gebert, Hanau (DE); Paul Schuster, St. Paul, MN (US); Lisa Meyer, Hanau (DE)

(73) Assignees: Heraeus Medical Components LLC, St. Paul, MN (US); Heraeus Deutschland GmbH & Co. KG, Hanau (DE)

( * ) Notice: Subject to any disclaimer, the term of this patent is extended or adjusted under 35 U.S.C. 154(b) by 884 days.

(21) Appl. No.: 16/929,865

(22) Filed: Jul. 15, 2020

(65) Prior Publication Data
US 2021/0020335 A1    Jan. 21, 2021

Related U.S. Application Data

(60) Provisional application No. 62/879,099, filed on Jul. 26, 2019, provisional application No. 62/874,730, filed on Jul. 16, 2019.

(51) Int. Cl.
*B05D 3/06*    (2006.01)
*A61B 5/00*    (2006.01)
(Continued)

(52) U.S. Cl.
CPC ....... *H01B 13/003* (2013.01); *A61B 5/14865* (2013.01); *A61B 5/686* (2013.01);
(Continued)

(58) Field of Classification Search
None
See application file for complete search history.

(56) References Cited

U.S. PATENT DOCUMENTS

| | | |
|---|---|---|
| 9,131,885 B2 | 9/2015 | Simpson et al. |
| 9,450,022 B1 | 9/2016 | Wheeler et al. |

(Continued)

FOREIGN PATENT DOCUMENTS

| | | |
|---|---|---|
| WO | 2011/002025 | 1/2011 |
| WO | 2011/003035 | 1/2011 |
| WO | 2017/031197 | 2/2017 |

*Primary Examiner* — Binh X Tran
*Assistant Examiner* — Bradford M Gates
(74) *Attorney, Agent, or Firm* — Dicke, Billig & Czaja, PLLC

(57) ABSTRACT

One aspect relates to a process for preparing a processed filament, including provision of a filament, including a segment. At least in the segment, the filament includes a core, including a first metal, a first layer which is superimposed on the core, and includes a polymer, and a second layer which is superimposed on the first layer, and includes a second metal. The segment of the filament is processed by interaction of the segment with at least one beam of electromagnetic radiation of a first kind. The electromagnetic radiation of the first kind has a spectrum with a peak wavelength in the range from 430 to 780 nm. Further, one aspect relates to a processed filament, obtainable by the process; a filament; an electrical device, including at least a part of the processed filament.

13 Claims, 12 Drawing Sheets

(51) Int. Cl.
    *A61B 5/1486*     (2006.01)
    *B05D 7/00*     (2006.01)
    *B05D 7/14*     (2006.01)
    *B05D 7/20*     (2006.01)
    *B23K 26/06*     (2014.01)
    *B23K 26/0622*     (2014.01)
    *B23K 26/352*     (2014.01)
    *B23K 26/36*     (2014.01)
    *H01B 1/02*     (2006.01)
    *H01B 13/00*     (2006.01)
    *H01B 13/34*     (2006.01)
    *B23K 26/402*     (2014.01)
    *B23K 101/32*     (2006.01)
    *B23K 101/34*     (2006.01)

(52) U.S. Cl.
    CPC ............... *B05D 3/065* (2013.01); *B05D 7/14* (2013.01); *B05D 7/20* (2013.01); *B05D 7/54* (2013.01); *B23K 26/0622* (2015.10); *B23K 26/0624* (2015.10); *B23K 26/0626* (2013.01); *B23K 26/355* (2018.08); *B23K 26/36* (2013.01); *H01B 1/02* (2013.01); *H01B 13/348* (2013.01); *A61B 2562/12* (2013.01); *A61B 2562/125* (2013.01); *B23K 26/402* (2013.01); *B23K 2101/32* (2018.08); *B23K 2101/34* (2018.08)

(56) References Cited

U.S. PATENT DOCUMENTS

| | | | |
|---|---|---|---|
| 2011/0028816 A1* | 2/2011 | Simpson | A61B 5/14517 600/345 |
| 2014/0071595 A1* | 3/2014 | De Jong | C09J 5/02 361/679.01 |
| 2014/0088389 A1* | 3/2014 | Simpson | C12Q 1/002 600/345 |
| 2014/0262462 A1 | 9/2014 | Shah et al. | |
| 2017/0049349 A1 | 2/2017 | Sallee et al. | |
| 2019/0192220 A1* | 6/2019 | Margallo Balbás | A61B 18/02 |

\* cited by examiner

100

600

800

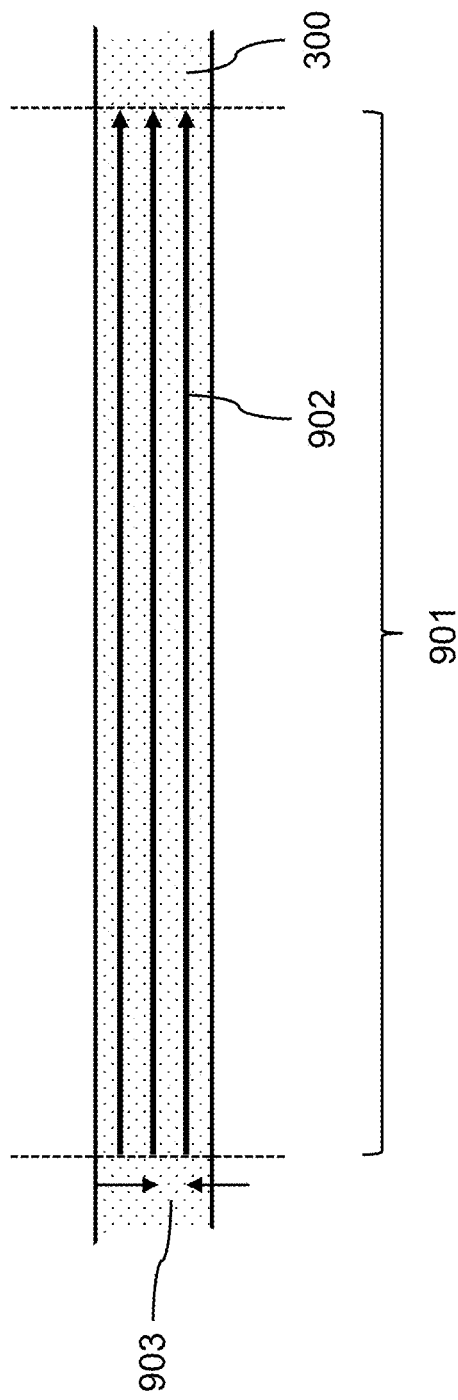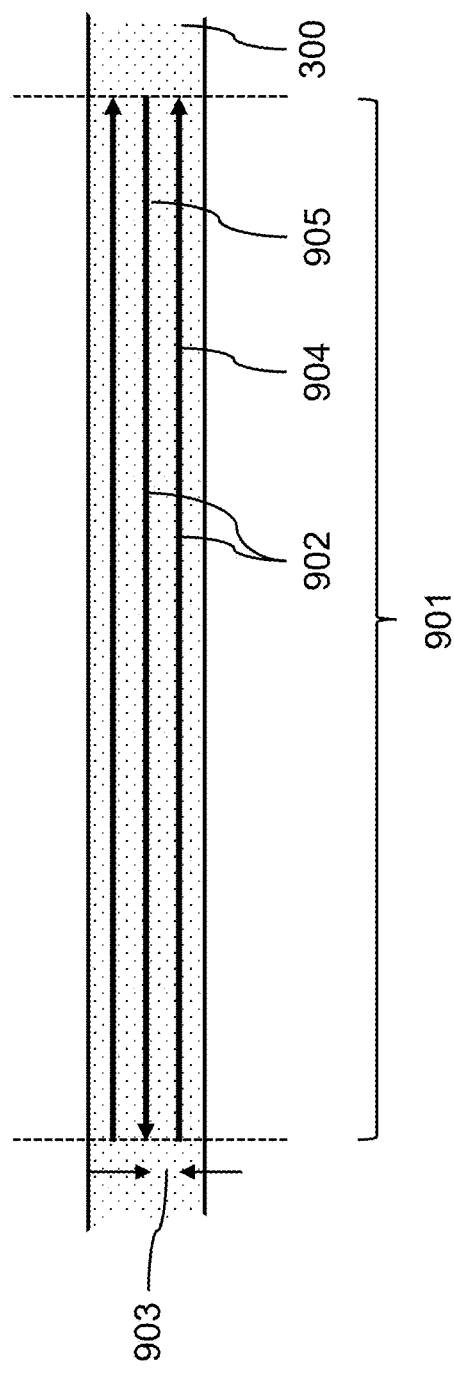

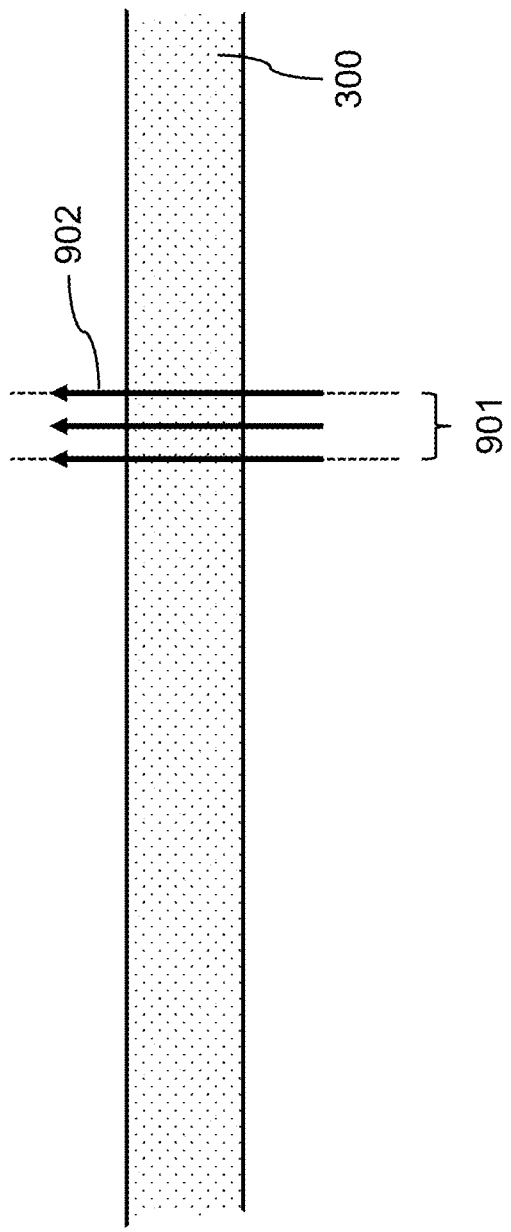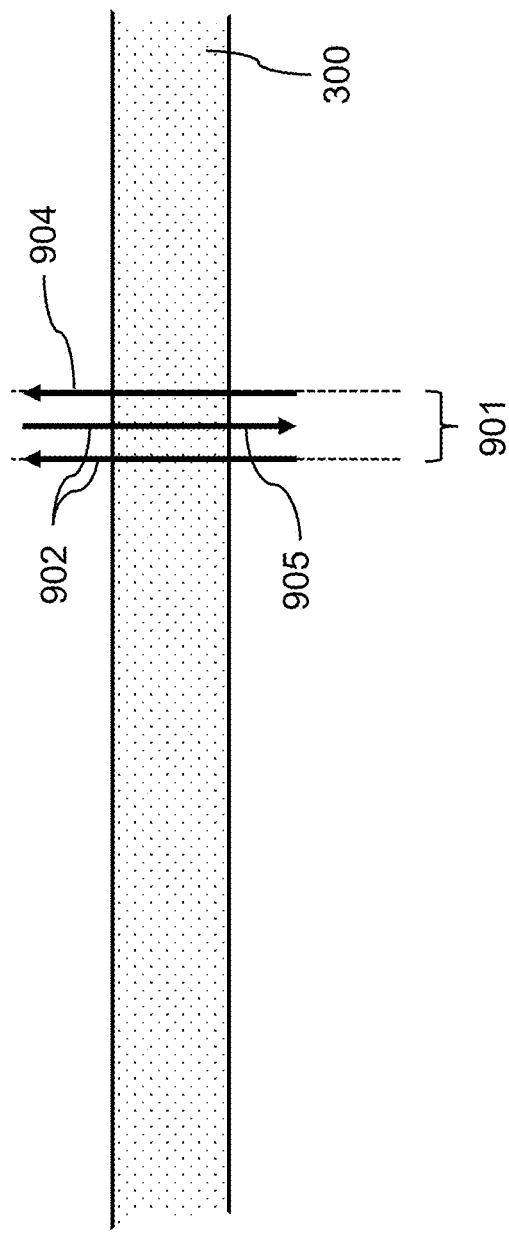

PROCESS FOR PREPARING A PROCESSED FILAMENT, INCLUDING INTERACTION OF A SEGMENT WITH AT LEAST ONE BEAM OF ELECTROMAGNETIC RADIATION OF A FIRST KIND

CROSS-REFERENCED TO RELATED APPLICATION

This Non-Provisional patent application claims the benefit of the filing date of U.S. Provisional Patent Application Ser. No. 62/874,730, filed Jul. 16, 2019, and U.S. Provisional Patent Application Ser. No. 62/879,099, filed Jul. 26, 2019, both of which are incorporated herein by reference.

TECHNICAL FIELD

One aspect relates to a process for preparing a processed filament.

SUMMARY

One aspect is process for preparing a processed filament including as steps
a) provision of a filament, including a segment,
   wherein, at least in the segment, the filament includes
   i) a core, including a first metal,
   ii) a first layer which
      I) is superimposed on the core, and
      II) includes a polymer, and
   iii) a second layer which
      I) is superimposed on the first layer, and
      II) includes a second metal; and
b) processing the segment of the filament by interaction of the segment with at least one beam of electromagnetic radiation of a first kind;
wherein the electromagnetic radiation of the first kind has a spectrum with a peak wavelength in the range from 430 to 780 nm. Further, one aspect relates to a processed filament, obtainable by the process; to a filament; to an electrical device, including at least a part of the processed filament or the filament; to a device for processing a filament; to a use of at least one laser of a first kind; and to a use of a filament.

BACKGROUND

Thin multilayer wires are used in applications such as electrochemical sensors. Such wires often include a metal core, a polymer coating and an outer metal coating. Preparing the wire for manufacture of an electrochemical sensor includes high-precision laser ablation of the outer metal layer across defined segments of the wire which are then coated with enzymes. The thin multilayer wires often have some degree of eccentricity which means that the outer metal layer is of non-uniform thickness around the wire circumference. A trade-off between ablating the outer metal layer as completely as possible on the one hand and avoiding damages to the PU-layer on the other hand results. In practice, the outer metal layer needs to be removed completely in the predetermined segments of the wire in order to allow for the preparation of electrochemical sensors. Considering possible damages to the PU-layer due to the laser ablation process, the overall thickness of the PU-layer may not be reduced beyond a minimum value in order to ensure an as thick as necessary PU-layer around the entire circumference of the wire. This determines a minimum diameter of the whole wire and, thus, sets a lower threshold to attempts of miniaturising the sensor. Further, damages to the PU-layer mean partial structuring of the outer PU-layer surface. This may lead to a non-uniform surface tension of the PU-layer's outer surface. Non-uniform enzyme coating thicknesses may be obtained. In the end, the signal-to-noise-ratio and the linearity of the sensor response may suffer.

Generally, it is an object of the present invention to at least partly overcome a disadvantage arising from the prior art.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The figures illustrate, in schematic form and not to scale, unless stated otherwise in the description or the respective figure:

FIG. 9a) an illustration of parallel uni-directional processing;

FIG. 9b) an illustration of parallel bi-directional processing;

FIG. 9c) an illustration of perpendicular uni-directional processing;

FIG. 9d) an illustration of perpendicular bi-directional processing;

DETAILED DESCRIPTION

Figure 1:
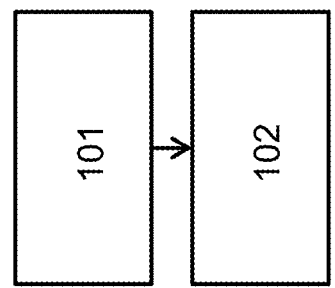
FIG. 1 a flow-chart of a process according to one embodiment.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

One aspect of one embodiment provides a device and/or a process for preparing a multilayer wire for manufacturing an as small as possible electrochemical sensor. This, in one embodiment, includes providing an as thin as possible multilayer wire for manufacturing the electrochemical sensor. A further aspect of one embodiment is providing a device and/or a process for preparing a multilayer wire for manufacturing an electrochemical sensor of as good as possible accuracy, in one embodiment in terms of a signal-to-noise-ratio of the sensor or a linearity of a sensor response or both. Further, it is an aspect of one embodiment to provide a device and/or a process for preparing a multilayer wire for manufacturing an electrochemical sensor, wherein a polymer layer of the wire or a metal core of the wire or both is as far as possible not damaged in the course of preparing the wire. According to a further aspect of one embodiment, one of the above advantageous processes and/or devices is provided, wherein the process/device is as simple as possible. It is a further aspect of one embodiment to provide a thin multilayer wire which is particularly suitable for manufacturing an electrochemical sensor that is characterised by one or more of the above advantages.

A contribution to at least one of the above objects is given by the independent claims. The dependent claims provides in one embodiment of the present invention which also serve solving at least one of the above mentioned objects.

A contribution to the solution of at least one of the above objects is provided by an embodiment 1 of a process, according to one embodiment, for preparing a processed filament, the process including as steps
 a) provision of a filament, including a segment,
  wherein, at least in the segment, in one embodiment over its entire length, the filament includes
   i) a core, including a first metal,
   ii) a first layer which
    I) is superimposed on the core, and
    II) includes a polymer, and
   iii) a second layer which
    I) is superimposed on the first layer, and
    II) includes a second metal; and
 b) processing the segment of the filament by interaction of the segment with at least one beam of electromagnetic radiation of a first kind;
wherein the electromagnetic radiation of the first kind has a spectrum with a peak wavelength in the range from 430 to 780 nm, in one embodiment from 430 to 640 nm, in one embodiment from 430 to 600 nm, in one embodiment from 490 to 600 nm, and in one embodiment from 490 to 570 nm, in one embodiment from 500 to 560 nm, in one embodiment from 510 to 550 nm, in one embodiment from 520 to 540 nm, in one embodiment from 525 to 540 nm, and in one embodiment from 528 to 536 nm.

Herein, process steps which follow one another in the order of the characters denoting the steps may follow one another directly or indirectly in time, i.e. there may be a further process step in-between or not. Further, the process steps, which follow one another in the order of the characters denoting the steps, may be conducted one after the other, in partial temporal overlap or simultaneously. After the step b), in one embodiment after the step c), the process, in one embodiment, includes a further step of creating an image, in one embodiment a sequence of images, of the segment of the processed filament. This further step, in one embodiment, includes capturing the image, in one embodiment the sequence of images, of the segment of the processed filament.

In its embodiment 2, the inventive process is configured according to its embodiment 1, wherein a surface of the first layer has an average roughness $R_a$ in the range from 0.07 to 4 μm, in one embodiment from 0.1 to 2 μm, and in one embodiment from 0.2 to 1.2 μm.

In its embodiment 3, the inventive process is configured according to its embodiment 1 or 2, wherein a surface of the first layer has a root-mean-squared roughness $R_q$ in the range from 0.2 to 7 μm, in one embodiment from 0.5 to 4 μm, and in one embodiment from 1 to 3.5 μm.

In its embodiment 4, the inventive process is configured according to any of its preceding embodiments, wherein the surface of the first layer faces the second layer. This means that the surface, in one embodiment, is an outer surface of the first layer. In one embodiment, the surface is at least part of a lateral surface of the first layer. In one embodiment, the surface represents 50 to 100%, in one embodiment 60 to 100%, in one embodiment 70 to 100%, in one embodiment 80 to 100%, in one embodiment 90 to 100%, and in one embodiment 95 to 100%, of an overall outer lateral surface of the first layer.

In its embodiment 5, the inventive process is configured according to any of its preceding embodiments, wherein the second metal is different from the first metal.

In its embodiment 6, the inventive process is configured according to any of its preceding embodiments, wherein the at least one beam of electromagnetic radiation of the first kind is at least one laser beam of a first kind.

In its embodiment 7, the inventive process is configured according to its embodiment 6, wherein the at least one laser beam of the first kind is at least one pulsed laser beam of the first kind, as opposed to at least one continuous layer beam.

In its embodiment 8, the inventive process is configured according to its embodiment 7, wherein the at least one pulsed laser beam of the first kind is characterised by a pulse duration in a range from 10 fs to 500 ns, in one embodiment from 50 fs to 400 ns, in one embodiment from 100 fs to 300 ns, in one embodiment from 500 fs to 200 ns, in one embodiment from 1 to 100 ns, in one embodiment from 10 to 100 ns, and in one embodiment from 15 to 80 ns.

In its embodiment 9, the inventive process is configured according to its embodiment 7 or 8, wherein a fluence of the at least one pulsed laser beam of the first kind is in the range from 1.0 to 5.0 J/cm² per pulse, in one embodiment from 1.5 to 4.5 J/cm² per pulse, in one embodiment from 2.0 to 4.0 J/cm² per pulse, and in one embodiment from 2.5 to 3.8 J/cm² per pulse.

In one embodiment, in the process step b) a spot of the at least one beam of electromagnetic radiation of the first kind is moved across the segment. Further in one embodiment, this spot is of a size in the range from 5 to 50 μm, in one embodiment 5 to 40 μm, in one embodiment 5 to 30 μm, and in one embodiment 10 to 20 μm. In one embodiment, the preceding size is the length of a diameter of the spot. A preferred spot is a focal spot. Further in one embodiment, the spot is about circular.

In its embodiment 10, the inventive process is configured according to any of its embodiments 7 to 9, wherein the at least one pulsed laser beam of the first kind is characterised by an energy per pulse in the range from 2 to 15 μJ, in one embodiment from 2 to 13 μJ, in one embodiment from 3 to 10 μJ, and in one embodiment from 4 to 8 μJ.

In its embodiment 11, the inventive process is configured according to any of its embodiments 7 to 10, wherein the at least one pulsed laser beam of the first kind is pulsed at a frequency in the range from 5 to 600 kHz, in one embodiment from 10 to 500 kHz, in one embodiment from 20 to 500 kHz, in one embodiment from 30 to 450 kHz, in one embodiment from 40 to 400 kHz, in one embodiment from 50 to 350 kHz, in one embodiment from 80 to 300 kHz, in one embodiment from 90 to 250 kHz, in one embodiment from 100 to 200 kHz, and in one embodiment from 110 to 190 kHz.

In its embodiment 12, the inventive process is configured according to any of its embodiments 6 to 11, wherein the at least one laser beam of the first kind is obtainable from at least one solid-state laser. A gain medium of the at least one solid-state laser is, in one embodiment, a crystal. A preferred crystal is doped with neodym. A preferred neodym-doped crystal includes yttrium. A preferred crystal which includes yttrium is selected from the group consisting of Nd:YAG, Nd:Y3A15,012, and Nd:YVO4. Therein, Nd:YVO4 is particularly preferred.

In its embodiment 13, the inventive process is configured according to any of its preceding embodiments, wherein, in the step b), the processing includes sweeping a spot of the at least one beam of electromagnetic radiation of the first kind across a surface of the segment in a first multitude of linear sweeps. The spot of the at least one beam of electromagnetic radiation of the first kind is, in one embodiment, a focal spot of this at least one beam. In case of more than one beam, there may be more than one spot. In this embodiment, the spot is moved across the surface of the segment in a sequence of straight lines (first multitude of linear sweeps), thereby scanning the surface with the at least one beam of electromagnetic radiation of the first kind. Hence, each linear sweep represents a straight line. Here, the surface of the segment is, in one embodiment, an outer surface of the second layer. The surface may be an entire outer surface of the segment or part of the overall outer surface of the segment.

In its embodiment 14, the inventive process is configured according to its embodiment 13, wherein the linear sweeps of the first multitude of linear sweeps are conducted in the same direction. This case is also referred to as uni-directional processing.

In its embodiment 15, the inventive process is configured according to its embodiment 13, wherein a first fraction of the linear sweeps of the first multitude of linear sweeps is conducted in a first direction, wherein a further fraction of the linear sweeps of the first multitude of linear sweeps is conducted in a further direction, wherein the further direction is opposite to the first direction. This case is also referred to as bi-directional processing.

In its embodiment 16, the inventive process is configured according to any of its embodiments 13 to 15, wherein the linear sweeps of the first multitude of linear sweeps incline angles with a length of the filament, as oriented in the segment, in the range from 0 to 30°, in one embodiment from 0 to 20°, in one embodiment from 0 to 10°, and in one embodiment from 0 to 5°. In one embodiment the linear sweeps of the first multitude of linear sweeps are parallel to the length of the filament, as oriented in the segment.

In its embodiment 17, the inventive process is configured according to any of its embodiments 13 to 15, wherein the linear sweeps of the first multitude of linear sweeps incline angles with a length of the filament, as oriented in the segment, in the range from 60 to 90°, in one embodiment from 70 to 90°, in one embodiment from 80 to 90°, and in one embodiment from 85 to 90°. In one embodiment the linear sweeps of the first multitude of linear sweeps are perpendicular to the length of the filament, as oriented in the segment.

In its embodiment 18, the inventive process is configured according to any of its embodiments 13 to 17, wherein a distance between the linear sweeps of the first multitude of linear sweeps is in the range from 5 to 50 µm, in one embodiment from 5 to 40 µm, in one embodiment from 5 to 30 µm, in one embodiment from 8 to 20 µm, and in one embodiment from 10 to 20 µm. This distance is determined in a centre-to-centre manner. In the technical field, this distance is often also referred to as pitch.

In its embodiment 19, the inventive process is configured according to any of its embodiments 13 to 18, wherein, in the sweeping of the step b), the spot moves relative to the surface of the segment at a velocity in the range from 100 to 3000 mm/s, in one embodiment from 200 to 2500 mm/s, in one embodiment from 400 to 2000 mm/s, in one embodiment from 600 to 1800 mm/s, and in one embodiment from 800 to 1600 mm/s.

In its embodiment 20, the inventive process is configured according to any of its embodiments 13 to 19, wherein in the first multitude of linear sweeps the spot of the at least one beam of electromagnetic radiation of the first kind sweeps across each position on the surface of the segment at least once. Hence, in this embodiment, the first multitude of linear sweeps covers the entire surface of the segment. In other words, in the first multitude of linear sweeps, the at least one beam of electromagnetic radiation of the first kind scans the entire surface of the segment.

In its embodiment 21, the inventive process is configured according to its embodiment 20, wherein, in the step b), the sweeping includes repeating the first multitude of linear sweeps 1 to 15 times, in one embodiment 1 to 10 times, in one embodiment 1 to 8 times, in one embodiment 2 to 7 times, and in one embodiment 2 to 5 times.

In its embodiment 22, the inventive process is configured according to any of its preceding embodiments, wherein, in the step b), the processing is a subtractive process, as opposed to an additive process, such as welding.

In its embodiment 23, the inventive process is configured according to any of its preceding embodiments, wherein, in the step b), the processing includes at least partially, in one embodiment completely, removing the second layer from the segment of the filament. In one embodiment, in the step b), the processing includes at least partially, in one embodiment completely, removing the second layer from circumferentially around the segment of the filament.

In its embodiment 24, the inventive process is configured according to its embodiment 23, wherein, in the step b), at least partially, in one embodiment completely, removing the second layer from the segment of the filament includes ablation. Ablation is removal of material from the surface of an object by vaporisation, chipping, or other erosive processes. A preferred ablation is laser-ablation.

In its embodiment 25, the inventive process is configured according to any of its preceding embodiments, wherein the process includes a further step c) further processing the segment of the filament by interaction of the segment with at least one beam of electromagnetic radiation of a further kind.

In one embodiment, the at least one beam of electromagnetic radiation of the further kind is different from the at least one beam of electromagnetic radiation of the first kind. In one embodiment, the at least one beam of electromagnetic radiation of the further kind differs from the at least one beam of electromagnetic radiation of the first kind by one selected from the group consisting of a spectrum, in one embodiment a peak wavelength of the spectrum; a fluence; a pulse duration; a frequency of pulsing; an energy per pulse; and a focal spot size; or by a combination of at least two of these.

In its embodiment 26, the inventive process is configured according to its embodiment 25, wherein the electromagnetic radiation of the further kind has spectrum with a peak wavelength in the range from 10 to 430 nm, in one embodiment from 100 to 430 nm, in one embodiment from 150 to 430 nm, in one embodiment from 180 to 400 nm, in one embodiment from 200 to 400 nm, in one embodiment from 220 to 400 nm, and in one embodiment from 220 to 380 nm. A particularly preferred electromagnetic radiation of the further kind has spectrum with a peak wavelength in the range from 220 to 280 nm, in one embodiment from 230 to 260 nm; or from 300 to 400 nm, and in one embodiment from 330 to 380 nm.

In its embodiment 27, the inventive process is configured according to its embodiment 25 or 26, wherein the at least one beam of electromagnetic radiation of the further kind is at least one laser beam of a further kind.

In its embodiment 28, the inventive process is configured according to its embodiment 27, wherein the at least one laser beam of the further kind is at least one pulsed laser beam of the further kind.

In its embodiment 29, the inventive process is configured according to its embodiment 28, wherein the at least one pulsed laser beam of the further kind is characterised by a pulse duration in a range from 10 fs to 500 ns, in one embodiment from 50 fs to 400 ns, in one embodiment from 100 fs to 300 ns, in one embodiment from 500 fs to 200 ns, in one embodiment from 1 ns to 100 ns, in one embodiment from 1 to 50 ns, in one embodiment from 5 to 30 ns, and in one embodiment from 10 to 20 ns.

In its embodiment 30, the inventive process is configured according to its embodiment 28 or 29, wherein a fluence of the at least one pulsed laser beam of the further kind is in the range from 0.1 to 50.0 $J/cm^2$ per pulse, in one embodiment from 0.2 to 30.0 $J/cm^2$ per pulse, in one embodiment from 0.3 to 20.0 $J/cm^2$ per pulse. In one embodiment, the fluence of the at least one pulsed laser beam of the further kind is in the range from 0.1 to 50.0 $J/cm^2$ per pulse, in one embodiment from 0.2 to 30.0 $J/cm^2$ per pulse. In a further embodiment, the fluence of the at least one pulsed laser beam of the further kind is in the range from 1 to 20.0 $J/cm^2$ per pulse in one embodiment from 11 to 18 $J/cm^2$ per pulse, and in one embodiment from 12.0 to 17.0 $J/cm^2$ per pulse.

In one embodiment, in the process step c) a spot of the at least one beam of electromagnetic radiation of the further kind is moved across the segment. Further in one embodiment, this spot is of a size in the range from 2 to 50 µm, in one embodiment 2 to 40 µm, in one embodiment 5 to 30 µm, in one embodiment 5 to 20 µm, in one embodiment 5 to 15 µm. In one embodiment, the preceding size is the length of a diameter of the spot. A preferred spot is a focal spot. Further in one embodiment, the sport is about circular.

In its embodiment 31, the inventive process is configured according to any of its embodiments 28 to 30, wherein the at least one pulsed laser beam of the further kind is characterised by an energy per pulse in the range from 1 to 50 µJ, in one embodiment from 5 to 40 µJ, in one embodiment from 10 to 30 µJ, in one embodiment from 10 to 25 µJ, in one embodiment from 10 to 20 µJ, in one embodiment from 12 to 18 µJ, and in one embodiment from 14 to 16 µJ.

In its embodiment 32, the inventive process is configured according to any of its embodiments 28 to 31, wherein the at least one pulsed laser beam of the further kind is pulsed at a frequency in the range from 1 to 100 kHz, in one embodiment from 10 to 80 kHz, in one embodiment from 20 to 60 kHz.

In its embodiment 33, the inventive process is configured according to any of its embodiments 25 to 32, wherein the at least one beam of electromagnetic radiation of the further kind is obtainable from at least one further solid-state laser, or from an Excimer laser. A gain medium of the at least one further solid-state laser is, in one embodiment, a crystal. A preferred crystal is doped with neodym. A preferred neodym-doped crystal includes yttrium. A preferred crystal which includes yttrium is selected from the group consisting of Nd:YAG, Nd:Y3A15,012, and Nd:YVO4. Therein, Nd:YVO4 is particularly preferred. A preferred Excimer laser includes a gain medium selected from the group consisting of $F_2$, ArF, KrF, XeCl-laser, and XeF, or a combination of at least two thereof. Therein, KrF is particularly preferred.

In its embodiment 34, the inventive process is configured according to any of its embodiments 25 to 33, wherein, in the step c), the further processing includes sweeping a spot of the at least one beam of electromagnetic radiation of the further kind across a surface of the segment in a further multitude of linear sweeps. In case of more than one beam, there may be more than one spot. In this embodiment, the spot is moved across the surface of the segment in a sequence of straight lines (further multitude of linear sweeps), thereby scanning the surface with the at least one beam of electromagnetic radiation of the further kind. Hence, each linear sweep represents a straight line. Here, the surface of the segment is, in one embodiment, an outer surface of the first layer. The surface may be an entire outer surface of the segment or part of the overall outer surface of the segment.

In its embodiment 35, the inventive process is configured according to its embodiment 34, wherein the linear sweeps of the further multitude of linear sweeps are conducted in the same direction.

In its embodiment 36, the inventive process is configured according to its embodiment 34, wherein a first fraction of the linear sweeps of the further multitude of linear sweeps is conducted in a first direction, wherein a further fraction of the linear sweeps of the further multitude of linear sweeps is conducted in a further direction, wherein the further direction is opposite to the first direction. Here, the first and further directions of step c) may be the same or different from the first and further directions of the step b).

In its embodiment 37, the inventive process is configured according to any of its embodiments 34 to 36, wherein the linear sweeps of the further multitude of linear sweeps incline angles with a length of the filament, as oriented in the segment, in the range from 0 to 30°, in one embodiment from 0 to 20°, in one embodiment from 0 to 10°, in one embodiment from 0 to 5°. In one embodiment the linear sweeps of the further multitude of linear sweeps are parallel to the length of the filament, as oriented in the segment.

In its embodiment 38, the inventive process is configured according to any of its embodiments 34 to 36, wherein the linear sweeps of the further multitude of linear sweeps incline angles with a length of the filament, as oriented in the segment, in the range from 60 to 90°, in one embodiment from 70 to 90°, in one embodiment from 80 to 90°, in one embodiment from 85 to 90°. In one embodiment the linear sweeps of the further multitude of linear sweeps are perpendicular to the length of the filament, as oriented in the segment.

In its embodiment 39, the inventive process is configured according to any of its embodiments 34 to 38, wherein a distance between the linear sweeps of the further multitude of linear sweeps is in the range from 1 to 50 µm, in one embodiment from 2 to 40 µm, in one embodiment from 3 to 30 µm, in one embodiment from 4 to 20 µm, in one embodiment from 5 to 15 µm. This distance is determined in a centre-to-centre manner. In the technical field, this distance is often also referred to as pitch.

In its embodiment 40, the inventive process is configured according to any of its embodiments 34 to 39, wherein, in the sweeping of the step c), the spot moves relative to the surface of the segment at a velocity in the range from 10 to 3000 mm/s, in one embodiment from 50 to 2000 mm/s, in one embodiment from 100 to 1800 mm/s, in one embodiment from 100 to 1600 mm/s, in one embodiment from 100 to 1000 mm/s, in one embodiment from 150 to 800 mm/s, and one embodiment from 200 to 600 mm/s.

In its embodiment 41, the inventive process is configured according to any of its embodiments 34 to 40, wherein in the further multitude of linear sweeps the spot of the at least one beam of electromagnetic radiation of the further kind sweeps across each position on the surface of the segment at least once. Hence, in this embodiment, the further multitude of linear sweeps covers the entire surface of the segment. In other words, in the further multitude of linear sweeps, the at least one beam of electromagnetic radiation of the further kind scans the entire surface of the segment.

In its embodiment 42, the inventive process is configured according to its embodiment 41, wherein, in the step c), the sweeping includes repeating the further multitude of linear sweeps 1 to 15 times, in one embodiment 1 to 10 times, in one embodiment 1 to 8 times, in one embodiment 2 to 7 times, and in one embodiment 1 to 5 times.

In its embodiment 43, the inventive process is configured according to any of its embodiments 25 to 42, wherein, in the step c), the further processing is a subtractive process.

In its embodiment 44, the inventive process is configured according to any of its embodiments 25 to 43, wherein, in the step c), the further processing includes at least partially, in one embodiment completely, removing the first layer from the segment of the filament. In one embodiment, in the step c), the further processing includes at least partially, in one embodiment completely, removing the first layer from circumferentially around the segment of the filament.

In its embodiment 45, the inventive process is configured according to its embodiment 44, wherein, in the step c), at least partially, in one embodiment completely, removing the first layer from the segment of the filament includes ablation.

In its embodiment 46, the inventive process is configured according to any of its preceding embodiments, wherein a surface of the core is characterised by
  A) an average roughness which is less, in one embodiment at least by a factor 0.1, than the average roughness $R_a$ of the surface of the first layer
  B) a root-mean-squared roughness which is less, in one embodiment at least by a factor 0.1, than the root-mean-squared roughness $R_q$ of the surface of the first layer, or
  C) both of A) and B).

In one embodiment, the average roughness of the surface of the core is in the range from 0.001 to 0.1 µm, in one embodiment from 0.005 to 0.05 µm, in one embodiment from 0.01 to 0.05 µm. Additionally or alternatively preferred, the root-mean-squared roughness of the surface of the core is in the range from 0.001 to 0.1 µm, in one embodiment from 0.006 to 0.06 µm, in one embodiment from 0.02 to 0.06 µm. The preceding surface of the core is, in one embodiment, at least part of a lateral surface of the core. In one embodiment, the surface represents 50 to 100%, in one embodiment 60 to 100%, in one embodiment 70 to 100%, in one embodiment 80 to 100%, in one embodiment 90 to 100%, and in one embodiment 95 to 100%, of an overall lateral surface of the core.

In its embodiment 47, the inventive process is configured according to any of its preceding embodiments, wherein the filament has a length in range from 10 m to 10 km, in one embodiment from 100 to 8 km, in one embodiment from 500 m to 5 km.

In its embodiment 48, the inventive process is configured according to any of its preceding embodiments, wherein the filament has a diameter in the range from 0.1 to 1.0 mm, in one embodiment from 0.1 to 0.8 mm, in one embodiment from 0.1 to 0.6 mm, and in one embodiment from 0.12 to 0.4 mm.

In its embodiment 49, the inventive process is configured according to any of its preceding embodiments, wherein the filament is one selected from the group consisting of a wire, a cable, and a fibre, or a combination of at least two thereof. A preferred fibre is an optical fibre. A particularly preferred filament is a wire.

In its embodiment 47, the inventive process is configured according to any of its preceding embodiments, wherein a thickness of the second layer is in the range from 1 to 25 µm, in one embodiment from 2 to 20 µm, in one embodiment from 3 to 17 µm, and in one embodiment from 5 to 15 µm.

In its embodiment 51, the inventive process is configured according to any of its preceding embodiments, wherein the first metal is one selected from the group consisting of platinum, tantalum, and palladium, or an alloy including one of the preceding metals. A preferred alloy including platinum is platinum iridium or platinum tungsten. A preferred alloy including tantalum is tantalum niobium or tantalum tungsten.

In its embodiment 52, the inventive process is configured according to any of its preceding embodiments, wherein the second metal is silver. In one embodiment, the second layer further includes a salt of the second metal. A preferred salt of silver is AgCl.

In its embodiment 53, the inventive process is configured according to any of its preceding embodiments, wherein the polymer is one selected from the group consisting of a poly-addition product, a poly-condensation product, and one or more polysiloxanes, or a combination of at least two thereof. A preferred poly-addition product is polyurethane or a polyolefin. A preferred poly-condensation product is one selected from the group consisting of polyimide, polyamide, and polyethylene terephthalate, or a combination of at least two thereof. A preferred polyolefin is polyethylene or polypropylene. A further preferred polymer is a thermoplastic polymer. A particularly preferred polymer is polyurethane.

In its embodiment 54, the inventive process is configured according to any of its preceding embodiments, wherein the processing of step b) does not include cutting the filament.

In its embodiment 55, the inventive process is configured according to any of its preceding embodiments, wherein, after the step b), in one embodiment after the step c), the process further includes a step of rolling up the segment of the on a take-up reel.

In its embodiment 56, the inventive process is configured according to any of its preceding embodiments, wherein, in the step a), the filament is provided in a feed reel.

In its embodiment 57, the inventive process is configured according to any of its preceding embodiments, wherein the process is performed as a reel-to-reel-process.

A further contribution to the solution of at least one of the above objects is provided by an embodiment 1 of a processed filament, according to one embodiment, obtainable by the inventive process according to any of its embodiments.

In its embodiment 2, the inventive processed filament is configured according to its embodiment 1, wherein the processed filament includes the segment, wherein in the segment
- a] a thickness of the second layer, and in one embodiment also a thickness of the first layer, is, in one embodiment circumferentially around the processed filament, less than outside the segment, or
- b] the second layer, and in one embodiment also the first layer, has been removed, in one embodiment circumferentially around the processed filament.

In its embodiment 3, the inventive processed filament is configured according to its embodiment 1 or 2, wherein the processed filament has a length in range from 10 m to 10 km, in one embodiment from 100 to 8 km, in one embodiment from 500 m to 5 km.

In its embodiment 4, the inventive processed filament is configured according to any of its preceding embodiments, wherein the processed filament is at least partially rolled up on a reel.

In its embodiment 5, the inventive processed filament is configured according to its embodiment 1 or 2, wherein the processed filament has a length in range from 0.5 to 5 cm, in one embodiment from 1 to 4 cm, in one embodiment from 1 to 3 cm.

In its embodiment 6, the inventive processed filament is configured according to any of its preceding embodiments, wherein the segment has a length in the range from 50 µm to 10 mm, in one embodiment from 100 µm to 10 mm, in one embodiment from 1 to 10 mm, and in one embodiment from 1 to 8 mm.

In its embodiment 4, the inventive processed filament is configured according to any of its preceding embodiments, wherein outside the segment a thickness of the second layer is in a range from 1 to 25 µm, in one embodiment from 2 to 20 µm, in one embodiment from 3 to 17 µm, and in one embodiment from 5 to 15 µm.

A further contribution to the solution of at least one of the above objects is provided by an embodiment 1 of a filament, according to one embodiment, including
- a. a core, including a first metal;
- b. a first layer which
  - i. is superimposed on the core, and
  - ii. includes a polymer; and
- c. a second layer which
  - i. is superimposed on the first layer, and
  - ii. includes a second metal;
- wherein a surface of the first layer is characterised by
  - a] an average roughness $R_a$ in the range from 0.07 to 4 µm, in one embodiment from 0.1 to 2 µm, in one embodiment from 0.2 to 1.2 µm, or
  - b] a root-mean-squared roughness $R_q$ in the range from 0.2 to 7 µm, in one embodiment from 0.5 to 4 µm, in one embodiment from 1 to 3.5 µm, or
  - c] both of a] and b];

wherein the filament includes a segment, in which
- a} a thickness of the second layer, and in one embodiment also a thickness of the first layer, is, in one embodiment circumferentially around the filament, less than outside the segment, or
- b} the second layer has been removed, in one embodiment circumferentially around the filament.

In its embodiment 2, the inventive filament is configured according to its embodiment 1, wherein the filament has a length in range from 10 m to 10 km, in one embodiment from 100 to 8 km, in one embodiment from 500 m to 5 km.

In its embodiment 3, the inventive filament is configured according to its embodiment 1 or 2, wherein the filament is at least partially rolled up on a reel.

In its embodiment 4, the inventive filament is configured according to its embodiment 1, wherein the filament has a length in range from 0.5 to 5 cm, in one embodiment from 1 to 4 cm, in one embodiment from 1 to 3 cm.

In its embodiment 5, the inventive filament is configured according to any of its preceding embodiments, wherein the segment has a length in the range from 50 µm to 10 mm, in one embodiment from 100 µm to 10 mm, in one embodiment from 1 to 10 mm, and in one embodiment from 1 to 8 mm.

In its embodiment 6, the inventive filament is configured according to any of its preceding embodiments, wherein outside the segment a thickness of the second layer is in a range from 1 to 25 µm, in one embodiment from 2 to 20 µm, in one embodiment from 3 to 17 µm, and in one embodiment from 5 to 15 µm.

A further contribution to the solution of at least one of the above objects is provided by an embodiment 1 of an electrical device, according to one embodiment, including at least a part of the inventive processed filament, or at least a part of the inventive filament, in each case according to any of its preceding embodiments, wherein the at least part includes the segment.

In its embodiment 2, the inventive electrical device is configured according to its embodiment 1, wherein the electrical device includes a sensor which includes the at least part of the processed filament. A preferred sensor is an electrochemical sensor.

In its embodiment 3, the inventive electrical device is configured according to its embodiment 1 or 2, wherein the electrical device is a medical device. A preferred medical device is an implantable medical device.

A further contribution to the solution of at least one of the above objects is provided by an embodiment 1 of a device, according to one embodiment, for processing a filament in a process stream, the device including as component a first source of at least one beam of electromagnetic radiation of a first kind, wherein the filament includes a segment, wherein, at least in the segment, in one embodiment over its entire length, the filament includes
- a} a core, including a first metal,
- b} a first layer which
  - i} is superimposed on the core, and
  - ii} includes a polymer, and
- c} a second layer which
  - i} is superimposed on the first layer, and
  - ii} includes a second metal, wherein the first source is designed and arranged to remove the second layer at least partially from the segment, in one embodiment from circumferentially around the segment, by interaction of the segment with the at least one beam of electromagnetic radiation of the first kind, wherein the electromagnetic radiation of the first kind has a spectrum with a peak wavelength in the range from 430 to 780 nm, in one embodiment from 430 to 640 nm, in one embodiment from 430 to 600 nm, in one embodiment from 490 to 600 nm, in one embodiment from 490 to 570 nm, in one embodiment from 500 to 560 nm, in one embodiment from 510 to 550 nm, in one embodiment from 520 to 540 nm, in one embodiment from 525 to 540 nm, and in one embodiment from 528 to 536 nm. In one embodiment, the device includes no means to cut the filament. The device, in one embodiment, further includes a means to focus the at least one beam of electromagnetic radiation of the first kind onto the segment of the filament. A preferred means to focus the at least one beam of electromagnetic radiation of the first kind is an optical system. A preferred optical system includes at least one focusing lens.

In one embodiment, the device includes an imaging means, designed and arranged to provide an image, in one embodiment a sequence of images, of the segment of the filament after having been processed by the at least one beam of electromagnetic radiation of the first kind and in one embodiment in addition by the at least one beam of electromagnetic radiation of the further kind. Accordingly, the imaging means is, in one embodiment, arranged down-stream, of the first source and in one embodiment also downstream of the further source. A preferred imaging means is an image capturing means. A preferred image capturing means is a camera. The image capturing means is designed and arranged for creating and recording an image, in one embodiment a sequence of images, of the segment of the processed filament.

In its embodiment 2, the inventive device is configured according to its embodiment 1, wherein the device includes a further source of at least one beam of electromagnetic radiation of a further kind, wherein the further source is
  a) arranged down-stream of the first source, and
  b) designed and arranged to remove the first layer at least partially, in one embodiment completely, from the segment, in one embodiment from circumferentially around the segment, by interaction of the segment with the at least one beam of electromagnetic radiation of the further kind,
wherein the electromagnetic radiation of the further kind has spectrum with a peak wavelength in the range from 10 to 430 nm, in one embodiment from 100 to 430 nm, in one embodiment from 150 to 430 nm, in one embodiment from 180 to 400 nm, in one embodiment from 200 to 400 nm, in one embodiment from 220 to 400 nm, and in one embodiment from 220 to 380 nm. A particularly preferred electromagnetic radiation of the further kind has spectrum with a peak wavelength in the range from 220 to 280 nm, in one embodiment from 230 to 260 nm; or from 300 to 400 nm, in one embodiment from 330 to 380 nm. The device, in one embodiment, further includes a means to focus the at least one beam of electromagnetic radiation of the further kind onto the segment of the filament. A preferred means to focus the at least one beam of electromagnetic radiation of the further kind is an optical system. A preferred such optical system includes at least one focusing lens.

In its embodiment 3, the inventive device is configured according to its embodiment 1 or 2, wherein a surface of the first layer is characterised by
  A) an average roughness $R_a$ in the range from 0.07 to 4 µm, in one embodiment from 0.1 to 2 µm, in one embodiment from 0.2 to 1.2 µm, or
  B) a root-mean-squared roughness $R_q$ in the range from 0.2 to 7 µm, in one embodiment from 0.5 to 4 µm, in one embodiment from 1 to 3.5 µm, or
  C) both of A) and B).

In its embodiment 4, the inventive device is configured according to any of its preceding embodiments, wherein a surface of the core is characterised by
  A) an average roughness in the range from 0.001 to 0.1 µm, in one embodiment from 0.005 to 0.05 µm, in one embodiment from 0.01 to 0.05 µm, or
  B) a root-mean-squared roughness in the range from 0.001 to 0.1 µm, in one embodiment from 0.006 to 0.06 µm, in one embodiment from 0.02 to 0.06 µm, or
  C) both of A) and B).

The preceding surface of the core is, in one embodiment, at least part of a lateral surface of the core. In one embodiment, the surface represents 50 to 100%, in one embodiment 60 to 100%, in one embodiment 70 to 100%, in one embodiment 80 to 100%, in one embodiment 90 to 100%, and in one embodiment 95 to 100%, of an overall lateral surface of the core.

In its embodiment 5, the inventive device is configured according to any of its preceding embodiments, wherein the first source is at least one laser of a first kind. A preferred laser of the first kind is a solid-state laser. A gain medium of this solid-state laser is, in one embodiment, a crystal. A preferred crystal is doped with neodym. A preferred neodym-doped crystal includes yttrium. A preferred crystal which includes yttrium is selected from the group consisting of Nd:YAG, Nd:Y3A15,012, and Nd:YVO4. Therein, Nd:YVO4 is particularly preferred.

In its embodiment 6, the inventive device is configured according to any of its preceding embodiments, wherein the further source is at least one laser of a further kind. A preferred laser of the further kind is a solid-state laser or an Excimer laser. A gain medium of this solid-state laser is, in one embodiment, a crystal. A preferred crystal is doped with neodym. A preferred neodym-doped crystal includes yttrium. A preferred crystal which includes yttrium is selected from the group consisting of Nd:YAG, Nd:Y3A15, 012, and Nd:YVO4. Therein, Nd:YVO4 is particularly preferred. A preferred Excimer laser includes a gain medium selected from the group consisting of $F_2$, ArF, KrF, XeCl-laser, and XeF, or a combination of at least two thereof. Therein, KrF is particularly preferred.

In its embodiment 7, the inventive device is configured according to any of its preceding embodiments, wherein the device further includes a guiding means, including a filament feed which is arranged upstream of the first source, and designed to feed the filament from a feed reel. Here, the guiding means may include the feed reel or not.

In its embodiment 8, the inventive device is configured according to its embodiment 7, wherein the device includes the feed reel.

In its embodiment 9, the inventive device is configured according to its embodiment 7 or 8, wherein the guiding means further includes a filament take-up means which is arranged down-stream of the first source, in one embodiment also of the further source. In one embodiment, between the filament feed and the filament take-up means, the device includes no means to cut the filament.

In its embodiment 10, the inventive device is configured according to its embodiment 9, wherein the filament take-up means is designed for the processed filament to be rolled up on a take-up reel. Here, the guiding means may include the take-up reel or not.

In its embodiment 11, the inventive device is configured according to any of its preceding embodiments, wherein the device is designed for a reel-to-reel-processing of the filament.

In its embodiment 12, the inventive device is configured according to any of its embodiments 7 to 11, wherein the guiding means further includes a first tension control means which is arranged up-stream of the first source, wherein the first tension control means is designed and arranged to adapt a tension of the segment of the filament during the processing. In one embodiment, the first tension control means is arranged between the filament feed and the first source.

In its embodiment 13, the inventive device is configured according to its embodiment 12, wherein the first tension control means includes a first multitude of deflection rollers.

In its embodiment 14, the inventive device is configured according to any of its preceding embodiments, wherein the guiding means further includes a further tension control means which is arranged down-stream of the first source, in one embodiment also of the further source, wherein the further tension control means is designed and arranged to adapt a tension of the segment of the filament during the processing. In one embodiment, the further tension control means is arranged between the first source and the filament take-up means, in one embodiment between the further source and the filament take-up means.

In its embodiment 15, the inventive device is configured according to its embodiment 14, wherein the further tension control means includes a further multitude of deflection rollers.

In its embodiment 16, the inventive device is configured according to any of its preceding embodiments, wherein the device includes the filament.

In its embodiment 17, the inventive device is configured according to its embodiment 16, wherein a first part of the filament is rolled up on the feed reel. The feed reel is, in one embodiment, arranged up-stream of the first source. In one embodiment, the segment is down-stream of the first part.

In its embodiment 18, the inventive device is configured according to its embodiment 16 or 17, wherein a further part of the filament is rolled up on the take-up reel. The take-up reel is, in one embodiment, arranged down-stream of the first source, in one embodiment also of the further source. In one embodiment, the segment is up-stream of the further part. Further preferred, the segment is between the first and the further part of the filament.

A further contribution to the solution of at least one of the above objects is provided by an embodiment 1 of a use 1, according to one embodiment, of at least one laser of a first kind for processing a segment of a filament by interaction of the segment with at least one beam of electromagnetic radiation of a first kind from the at least one laser of the first kind, wherein, at least in the segment, in one embodiment over its entire length, the filament includes
  a} a core, including a first metal,
  b} a first layer which
    i} is superimposed on the core, and
    ii} includes a polymer, and
  c} a second layer which
    i} is superimposed on the first layer, and
    ii} includes a second metal,
wherein the electromagnetic radiation of the first kind has a spectrum with a peak wavelength in the range from 430 to 780 nm, in one embodiment from 430 to 640 nm, in one embodiment from 430 to 600 nm, in one embodiment from 490 to 600 nm, in one embodiment from 490 to 570 nm, in one embodiment from 500 to 560 nm, in one embodiment from 510 to 550 nm, in one embodiment from 520 to 540 nm, in one embodiment from 525 to 540 nm, and in one embodiment from 528 to 536 nm.

In its embodiment 2, the inventive use 1 is configured according to its embodiment 1, wherein, in addition, at least one laser of a further kind is used for further processing the segment of the filament by interaction of the segment with at least one beam of electromagnetic radiation of a further kind from the at least one laser of the further kind, wherein the electromagnetic radiation of the further kind has spectrum with a peak wavelength in the range from 10 to 430 nm, in one embodiment from 100 to 430 nm, in one embodiment from 150 to 430 nm, in one embodiment from 180 to 400 nm, in one embodiment from 200 to 400 nm, in one embodiment from 220 to 400 nm, and in one embodiment from 220 to 380 nm. A particularly preferred electromagnetic radiation of the further kind has spectrum with a peak wavelength in the range from 220 to 280 nm, in one embodiment from 230 to 260 nm; or from 300 to 400 nm, in one embodiment from 330 to 380 nm.

A further contribution to the solution of at least one of the above objects is provided by an embodiment 1 of a use 2, according to one embodiment, of a filament for being processed by interaction of the filament with at least one beam of electromagnetic radiation of a first kind, wherein the electromagnetic radiation of the first kind has spectrum with a peak wavelength in the range from 430 to 780 nm, in one embodiment from 430 to 640 nm, in one embodiment from 430 to 600 nm, in one embodiment from 490 to 600 nm, in one embodiment from 490 to 570 nm, in one embodiment from 500 to 560 nm, in one embodiment from 510 to 550 nm, in one embodiment from 520 to 540 nm, in one embodiment from 525 to 540 nm, and in one embodiment from 528 to 536 nm, wherein the filament includes
  a} a core, including a first metal,
  b} a first layer which
    i} is superimposed on the core, and
    ii} includes a polymer, and
  c} a second layer which
    i} is superimposed on the first layer, and
    ii} includes a second metal.

In its embodiment 2, the inventive use 2 is configured according to its embodiment 1, wherein, in addition, the filament is used for being processed by interaction of the filament with at least one beam of electromagnetic radiation of a further kind, wherein the electromagnetic radiation of the further kind has spectrum with a peak wavelength in the range from 10 to 430 nm, in one embodiment from 100 to 430 nm, in one embodiment from 150 to 430 nm, in one embodiment from 180 to 400 nm, in one embodiment from 200 to 400 nm, in one embodiment from 220 to 400 nm, and in one embodiment from 220 to 380 nm. A particularly preferred electromagnetic radiation of the further kind has spectrum with a peak wavelength in the range from 220 to 280 nm, in one embodiment from 230 to 260 nm; or from 300 to 400 nm, in one embodiment from 330 to 380 nm.

In its embodiment 3, each of the inventive use 1 and 2 is configured according to any of its preceding embodiments, wherein a surface of the first layer is characterised by
  a] an average roughness $R_a$ in the range from 0.07 to 4 µm, in one embodiment from 0.1 to 2 µm, in one embodiment from 0.2 to 1.2 µm, or
  b] a root-mean-squared roughness $R_q$ in the range from 0.2 to 7 µm, in one embodiment from 0.5 to 4 µm, in one embodiment from 1 to 3.5 µm, or
  c] both of a] and b].

Features described as preferred in one category of one embodiment, such as the process or the device of one embodiment, are likewise preferred in a respective embodiment of the further categories of one embodiment, including the inventive filament and uses.

Filament

In the context of one embodiment, the filament may be any kind of filament which the skilled person deems appropriate. Herein, a filament is a linear, non-rigid element which has a length that is at least 10 times, in one embodiment at least 100 times, in one embodiment at least 1000 times, a diameter of the filament. Therein, "non-rigid" means that the filament is flexible at least to a degree which allows to reversibly roll the filament up on a roll without damaging the filament. In a cross-section which is perpendicular to the length of the filament, the filament may have any shape which the skilled person deems appropriate. In one embodiment, the filament has a cross-sectional shape, selected from the group consisting of circular, rectangular, oval, and elliptical, wherein a circular cross-section is particularly preferred. In one embodiment, the filament has the preceding cross-sectional shape over its full length. A particularly preferred filament is a wire.

Segment

The segment of the filament is a longitudinally extending portion of the filament, wherein a length of the segment is shorter than the length of the filament. In one embodiment, the length of the filament is at least 100 times, in one embodiment at least 1000 times, the length of the segment.

Structure of the Filament

The filament includes the core, the first layer which superimpose the core and the second layer which superimposes the first layer. Herein, the term "superimpose" means that the entities given may follow one another directly, in case of which they are in contact with each other, or indirectly, in case of which there is at least one further entity in-between. Hence, there may or may not be further layers between the core and the first layer and/or the first layer and the second layer. In one embodiment, the first layer is in contact with the core. Additionally or alternatively preferred, the second layer is on contact with the first layer. In each cross-section through the filament, which is perpendicular to the length of the filament, the core, in one embodiment, includes a geometric centre of the filament. Further, the second layer may be superimposed by a further layer on its outer side or not. In one embodiment, the second layer is not superimposed by any further layer on its outer side, i.e. the side which faces away from the core. Before processing the filament, the first layer, in one embodiment, superimposes the core over at least 50%, in one embodiment at least 60%, in one embodiment at least 70%, in one embodiment at least 80%, in one embodiment at least 90%, and in one embodiment 100%, in each case of an entire lateral surface of the core. Additionally or alternatively preferred, the second layer superimposes the first layer over at least 50%, in one embodiment at least 60%, in one embodiment at least 70%, in one embodiment at least 80%, in one embodiment at least 90%, and in one embodiment 100%, in each case of an entire lateral surface of the first layer, wherein this lateral surface faces away from the core. After processing the filament, the preceding holds, in one embodiment, outside of regions of the filament that have been processed. Hence, at least the segment of the processed filament is excluded from this specification. The core, in one embodiment, is of a shape of a cylinder which may have been bend (oblique cylinder). In one embodiment, the first layer or the second layer or both is of the shape of a hollow cylinder, respectively. Herein, the term cylinder does not restrict a cross-sectional shape. A preferred cylinder is a circular cylinder (circular cross-sectional shape) or a prism (polygonal cross-sectional shape). The core, the first layer and the second layer may be co-axial or not. In particular, the second layer is often not co-axial to the core and the first layer.

The core of the filament includes the first metal, in one embodiment, in a proportion in the range from 50 to 100 wt.-%, in one embodiment from 60 to 100 wt.-%, in one embodiment from 70 to 100 wt.-%, in one embodiment from 80 to 100 wt.-%, and in one embodiment from 90 to 100 wt.-%, in each case based on the weight of the core. A preferred first metal is biocompatible. In one embodiment, the overall core material is biocompatible. The first layer includes the polymer, in one embodiment, in a proportion in the range from 50 to 100 wt.-%, in one embodiment from 60 to 100 wt.-%, in one embodiment from 70 to 100 wt.-%, in one embodiment from 80 to 100 wt.-%, and in one embodiment from 90 to 100 wt.-%, in each case based on the weight of the first layer. In one embodiment, the polymer of the first layer, in one embodiment the overall material of the first layer is biocompatible. The second layer includes the second metal, in one embodiment, in a proportion in the range from 50 to 100 wt.-%, in one embodiment from 60 to 100 wt.-%, in one embodiment from 70 to 100 wt.-%, in one embodiment from 80 to 100 wt.-%, and in one embodiment from 90 to 100 wt.-%, in each case based on the weight of the second layer. In one embodiment, the second metal, in one embodiment the overall material of the second layer is biocompatible. In one embodiment, each of the materials of the filament defined herein is biocompatible. A preferred filament consists essentially of biocompatible materials. A preferred biocompatible material is one selected from the group consisting of biotolerant, bioinert and bioactive or a combination of at least two thereof. In one embodiment, the first metal or the second metal or both is a noble metal. In one embodiment, the first and second metals are different noble metals.

Peak Wavelength

The peak wavelength of a spectrum is a local maximum, in one embodiment in addition a global maximum, of the spectrum. A preferred peak wavelength is a laser wavelength, i.e. a main wavelength of a laser output. The laser wavelength may be a lasing wavelength of a gain medium of the laser or a wavelength which is obtained by a non-linear optical effect, such as frequency doubling, from the lasing wavelength.

Guiding Means

In the context of one embodiment, the guiding means may be any means which the skilled person deems suitable for guiding the filament such that the segment is arranged during the processing in a predetermined orientation. In general, the guiding means is one or more elements of the device according to one embodiment which defines an orientation of the segment during the processing. Further, the guiding means may define a fixation of the segment during processing or a tension of the segment during processing or both. The orientation of the segment may, for example, be achieved by an appropriate arrangement of the filament feed or the filament take-up means or both. Alternatively, the orientation of the segment during processing may be achieved by means of suitably arranged deflection rollers of the guiding means. Those deflection rollers may be part of the first and/or further tension control means.

Processing

In the context of one embodiment, the processing of the filament may be any kind of processing which the skilled person deems appropriate and which can be achieved by interaction of the at least one beam of electromagnetic radiation of the first kind, or of the at least one beam of electromagnetic radiation of the first and further kinds, in each case of with the segment of the filament. A preferred interaction is absorption. A particularly preferred processing includes removing part of the filament in the segment, in one embodiment by ablation, in one embodiment laser-ablation.

Reel-to-Reel-Processing

Reel-to-reel-processing means provision of the filament at least partially rolled up on a reel, at least partially unwinding the filament from the reel, then processing and then at least partially re-winding the processed filament on a further reel. In one embodiment, the filament is not cut in that process. Here, cutting means separating the filament into at least two distinct filaments.

Diameter

In case of a non-circular shape, such as a cross-section of the filament, the diameter of the shape is a length of a longest straight line which starts and ends on the edge of the shape.

Test Methods

The test methods which follow were utilized within the context of one embodiment. Unless stated otherwise, the measurements were conducted at an ambient temperature of 23° C., an ambient air pressure of 100 kPa (0.986 atm) and a relative air humidity of 50%.

Average Roughness $R_a$ and Root-Mean-Squared Roughness $R_q$

In order to determine the roughness of a surface of layer or of the core of the filament, a cross-section through the filament which is perpendicular to the filament length is prepared. The cross-section is polished prior to focused-ion-beam (FIB) inspection. An FIB image is assessed using suitable image editing software. Depending on the general cross-sectional shape of the surface to be examined, a suitable geometric form is drawn. In the case of a circular filament, a circle is drawn. The diameter of the circle is chosen to match the diameter of the surface to be examined in the cross-section. The position of the circle is fitted to the surface to be examined. The distance of the surface to the circle in radial direction is measured at 10 positions equidistantly around the circumference of the circle (see FIG. 11). The average roughness $R_a$ is obtained by calculating the arithmetic mean of the 10 distances, whereas the root-mean-squared roughness $R_q$ is obtained by calculating the root mean square of the 10 distances.

Spectrum and Peak Wavelength

In case of a laser beam as beam of electromagnetic radiation, the peak wavelength of the spectrum is the nominal peak wavelength of the laser output. This is either the wavelength at which the laser lases or, if a non-linear optical process is used to alter the output wavelength, the respective harmonic of the lasing wavelength. For example, a KrF-Excimer laser typically has a lasing wavelength at about 248 nm. A Nd:YVO4-laser typically has a lasing wavelength at about 1064 nm. If the light of the Nd:YVO4-laser is frequency doubled, the peak wavelength of the laser output is at about 532 nm. If the beam of electromagnetic radiation is not a laser beam, the spectrum of this electromagnetic radiation is measured using a spectrometer of the type CCS200 from Thorlabs GmbH. The measurement is conducted in accordance with the manufacturer's instructions. The peak wavelength of the measured spectrum is then a local maximum of the spectrum which is also its global maximum.

Pulse Frequency

The pulse Frequency is defined as the number of pulses, emitted per unit of time. The pulse frequency of a pulsed laser is adjusted at the device. Any pulse frequency, referred to herein, means the pulse frequency as adjusted at the device.

Pulse Duration

The pulse duration is defined as the time duration between the intensity levels of a pulse measured at FWHM (full width at half-maximum). It is measured with a suitable photo diode and an oscilloscope.

Fluence

The fluence is defined as energy per pulse [J]/effective focal spot area [$cm^2$]. Therein, the effective focal spot area is calculated as the area of a circle of a diameter which is the spot size according to the test method below.

Energy Per Pulse

The energy per pulse is determined by first measuring the accumulated energy of the beam over a period of irradiation of 1 second using a thermal power meter. If the focus of the beam is on the workpiece, this energy is measured right in front of the workpiece, i.e. slightly out of the focus point. The pulse frequency is determined as described above. The energy per pulse is calculated by dividing the accumulated energy by the pulse frequency in Hz.

Spot Size

The 2D-intensity distribution of the spot is measured using a 2D power meter. The spot size is determined by fitting a circle to the Full Width at half Maximum of the 2D-intensity distribution. The spot size is the diameter of this circle.

One embodiment is illustrated further by way of example hereinafter by examples and figures. The invention is neither restricted to the examples nor the figures.

In the comparative examples (not according to the invention) and the examples (according to one embodiment), wires of types A and B are processed as described below.

Preparation of Wires

Wires of types A and B, both which consist from the inside to the outside of a core of tantalum, a platinum layer, a polyurethane layer and a layer consisting of a mixture of silver and AgCl (Ag/AgCl-layer), are prepared as described in the following.

A wire precursor consisting of a core of tantalum and a cladding of platinum is prepared. This is effected by drawing a tube made of platinum on a rod made of tantalum. Further a conventional wire drawing method is applied to the wire precursor. This includes single die drawing (elongation per die 5 to 15%) the wire precursor at a drawing speed of about 10 m/min using lubrication oil. Ultrasonic cleaning and rinsing of the wire precursor are conducted in-line. Subsequently, an intermediate annealing step is conducted at an annealing temperature of 800° C. Therein, the wire precursor is moved through a furnace at an annealing speed of 20 m/min. Thereby, mechanical properties of the wire precursor are adjusted. Subsequently, multi die drawing (elongation per die 10 to 20%) is conducted at a drawing speed of 30 m/min using lubrication oil. Ultrasonic cleaning and rinsing of the wire precursor are conducted in-line. Further in-line, the wire precursor is coated with a resin of polyurethane. This is done by applying a wet film of the resin on the wire using enameling dies. Then the applied resin is dried thermally and the polymer is cured in an annealer. The applying, drying and curing steps are repeated 10 to 40 times in order to obtained a polyurethane layer thickness of about 20 μm. The polyurethane layer is coated in-line with an Ag/AgCl-layer.

This is done by applying a paste, which includes silver particles, AgCl, binder and solvent, to the polyurethane layer by enamel dies. The applied paste is dried thermally and cured. The steps of applying, drying and curing are repeated 2 to 10 times in order to obtain a 10 μm thick Ag/AgCl. In order to obtain wires of the type A, a paste with a fineness of grind (as defined in ASTM D1316) of about 3 μm (50 point) and about 5 μm (fourth continuous scratch), and a rather low temperature of about 200 to 260° C. is used for application of the Ag/AgCl layer. On the other hand, in order to obtain wires of the type B, the paste contains larger Ag/AgCl particles or particle agglomerates, having a fineness of grind (as defined in ASTM D1316) of about 12 to 5 μm (50 point) and about 12 to 20 μm (fourth continuous scratch). instead of the smaller particles defined above. Further, in order to prepare wires of the type B, a higher temperature of about 300 to 450° C. is used for application of the Ag/AgCl layer.

Fineness of grind as defined in ASTM D1316 is measured by dragging a paste through a wedge using a scraping tool, from the deep end to the shallow end, and the location of the fourth continuous scratch is measured at a scale. This value corresponds to the fourth-largest particle agglomerate size in the paste. Furthermore, the so-called "50 point" is measured at the location where half of the surface of the wedge is scratched.

Wire Processing

Example 1

Figure 6:
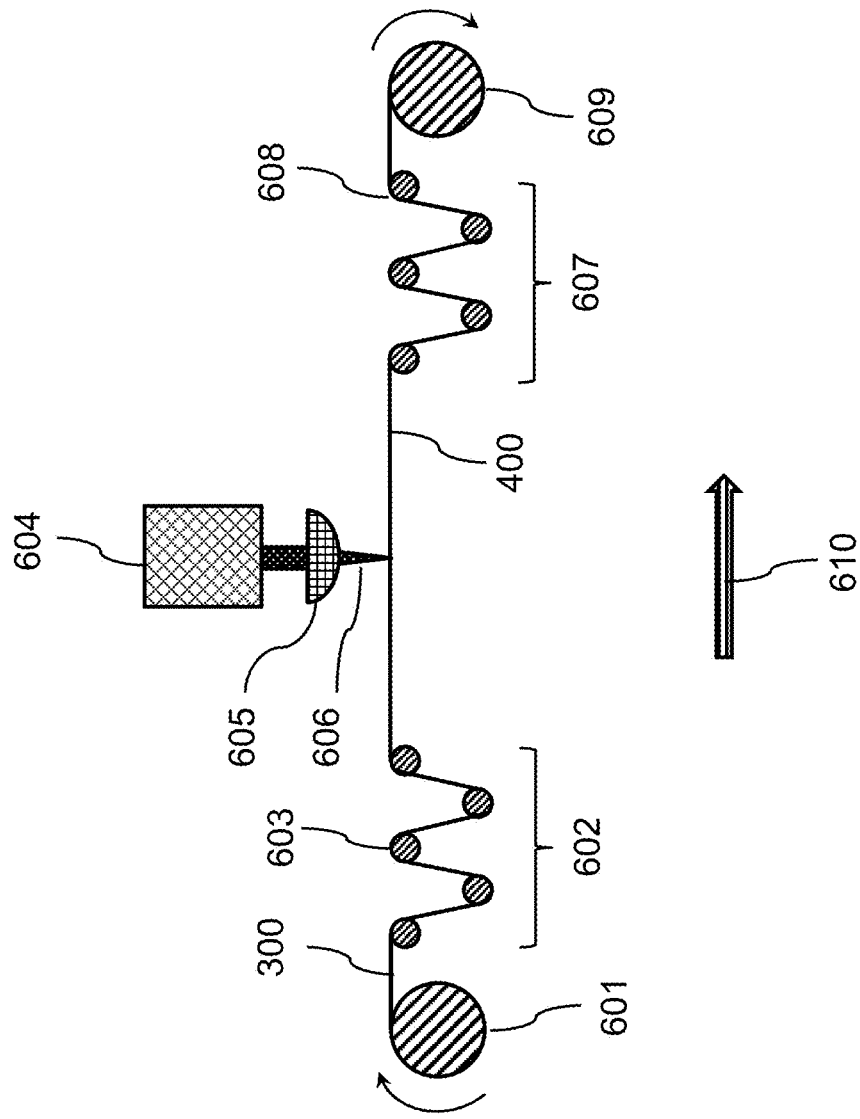
FIG. 6 a device according to one embodiment.

In the example 1, wires of type A are processed in a reel-to-reel fashion. A setup in accordance with FIG. 6 is used. Each 25 mm of the wire, an about 7 mm long segment of the wire is processed by completely laser-ablating the Ag/AgCl-layer from circumferentially around the wire. Therein, a Nd:YVO4-laser having a peak output wavelength at 532 nm is used. This output wavelength is obtained by frequency doubling the lasing wavelength of about 1064 nm of the Nd:YVO4-crystal. For the laser ablation, the laser is pulsed at a frequency of 160 kHz, wherein each pulse has an energy of 50 and a duration (width) of about 60 ns. The laser beam is focused down to a focal beam diameter of 15 μm on the wire surface. Each laser pulse has a fluence of 2.8 J/cm$^2$. The laser scans the segment from 4 sides circumferentially around the wire, one after the other. On each of the 4 sides the laser scans the wire in form of a multitude of lines/sweeps as illustrated in FIG. 9a). The lines of each multitude are uni-directional and parallel to the length of the wire. On each side, this scanning is repeated 4 times, i.e. on each of the 4 sides the wire is scanned in 5 passes by the laser. Therein, the scanning speed of the laser is about 1250 mm/s. The distance between the lines/sweeps (pitch) is about 13 μm.

Example 2

Example 2 is conducted as example 1, however, using wires of type B.

Comparative Example 1

In the comparative example 1, wires of type A are processed similar to example 1, however, using a KrF Excimer laser with laser wavelength at about 248 nm instead of the Nd:YVO4-laser.

Comparative Example 2

Comparative example 2 is conducted as Comparative example 1, however, using wires of type B.

Evaluation

Wires of types A and B are studied for the roughness of the outer lateral surface of the PU-layer in accordance with the methods described above in the test methods section. The average roughness $R_a$ of the outer lateral surface of the polyurethane layer (PU-layer) of type A wires is about 0.05 μm and the root-mean-squared roughness $R_q$ of about 0.1 μm. Wires of type B have an average roughness $R_a$ of the outer lateral surface of the polyurethane layer of about 0.7 μm and a root-mean-squared roughness $R_q$ of about 2.5 μm. Hence, the PU-layer of type A wires is rather smooth, whereas the PU-layer of type B wires is rather rough.

After having processed the wires as described above for the comparative examples and examples, the processed wires are studied under an optical microscope for the criteria given in the below table (see FIGS. 10a) to c)). The results of these studies are summarised in the below table. Therein, "−" means a result which is less favourable than "0", and "0" means a result which is less favourable than "+".

| | Ag/AgCl-layer ablated completely | Avoidance of damages to PU-layer | Avoidance of damages to Pt-layer |
|---|---|---|---|
| Comparative Example 1 | +/− | −/+ | 0/+ |
| Comparative Example 2 | +/− | −/+ | 0/+ |
| Example 1 | + | + | − |
| Example 2 | + | + | + |

The studies illustrate that, in wires as described above, the Ag/AgCl-layer is often not co-axial to the wire core and the PU-layer, i.e. often there is some eccentricity to the wire. In that case, the thickness of the Ag/AgCl-layer is not uniform around the circumference of the wire (see FIG. 3b)). Attempts to ablate the non-uniform Ag/AgCl-layer as completely as possible around the wire circumference tend to result in damages to the PU-layer underneath thinner regions of the Ag/AgCl-layer. In the above table, the results on the left-hand side of the slashes have been obtained with a focus on completely ablating the Ag/AgCl-layer, whereas the results on the right-hand side have been obtained with a focus on not damaging the PU-layer. It can be seen that, in the comparative examples, there is a trade-off between completely removing the Ag/AgCl-layer and avoiding damages to the PU-layer. In practice, the Ag/AgCl-layer needs to be removed completely. In order to adapt to the damages to the PU-layer, the latter needs be sufficiently thick. Further, damaging the PU-layer means to partially structure the outer surface of the PU-layer. In result, a surface tension of the outer surface of the PU-layer is not uniform across the exposed region of the PU-layer. In preparing an electrochemical sensor, this may lead to non-uniform coating thicknesses of enzyme layers on the wire. The signal-to-noise ratio of the sensor as well as the linearity of the sensor response may suffer in result.

The preceding trade-off is resolved in the inventive examples. In result, thinner PU-layer can be used. Thinner PU-layers render the overall wire thinner and, thus, allow for further densification of electrical components. Hence, electrical devices can be miniaturised further. This is particularly favourable in view of implantable medical devices, such as electrochemical sensors.

In addition to these advantages, example 2 avoids damages to the tantalum core and the platinum layer as far as possible while still removing the PU-layer completely. In consequence, further miniaturised electrical devices of high quality can be manufactured using wires that have been prepared in accordance with example 2.

Figure 3A:
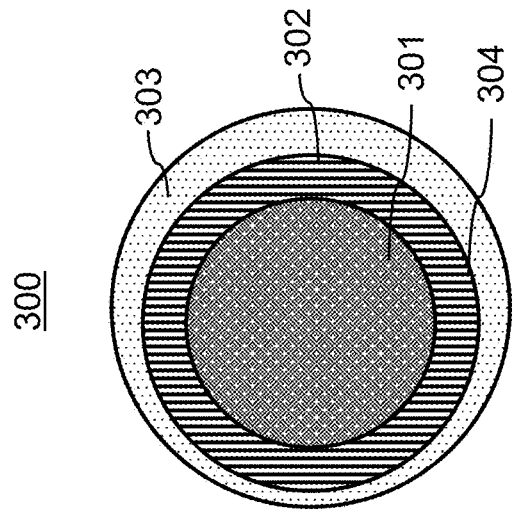
FIG. 3a) a cross-section through a filament.
Figure 4:
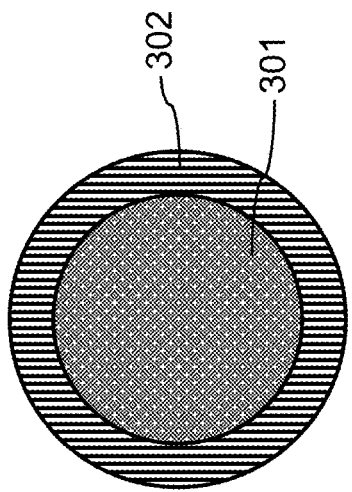
FIG. 4 a cross-section through a processed filament.

FIG. 1 illustrates a flow-chart of a process 100, according to one embodiment, for preparing a processed filament 400. The process 100 includes a process step a) 101 of providing a filament 300 which, over its entire length of 3 km, consists inside-out of a core 301, which is made from platinum; a first layer 302, which is coated onto the core 301 and made from a polyurethane; and a second layer 303 which is coated onto the first layer 302 and consists of a mixture of silver and AgCl. In a process step b) 102, a segment of the filament 300 is processed by interaction of the segment with a beam of electromagnetic radiation of a first kind 606 (see FIG. 6). The electromagnetic radiation of the first kind has a spectrum with a peak wavelength at 532 nm. The beam of electromagnetic radiation of the first kind 606 is a pulsed laser beam of a first kind. The laser beam of the first kind is pulsed at a frequency of 160 kHz, wherein each pulse has an energy of 5 µJ and a duration of about 60 ns. For completely laser-ablating the second layer 303 of the filament 300 in the segment, the laser beam of the first kind is focused down to a focal beam diameter of 15 µm. Each pulse has a fluence of 2.8 J/cm$^2$. A cross-section through the filament 300 is illustrated in FIG. 3a). A cross-section through the processed filament 400, obtained in the process step b) 102, is illustrated in FIG. 4. A device 600 for carrying out the process 100 of FIG. 1 is illustrated in FIG. 6.

Figure 2:
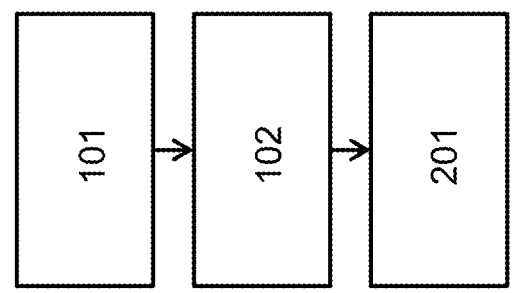
FIG. 2 a flow-chart of a further process according to one embodiment.
Figure 5:
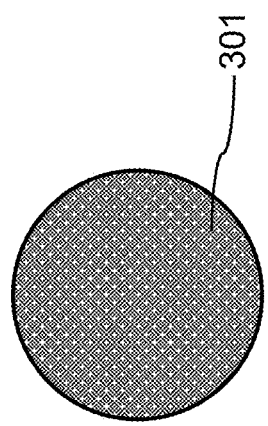
FIG. 5 a cross-section through a further processed filament.
Figure 7:
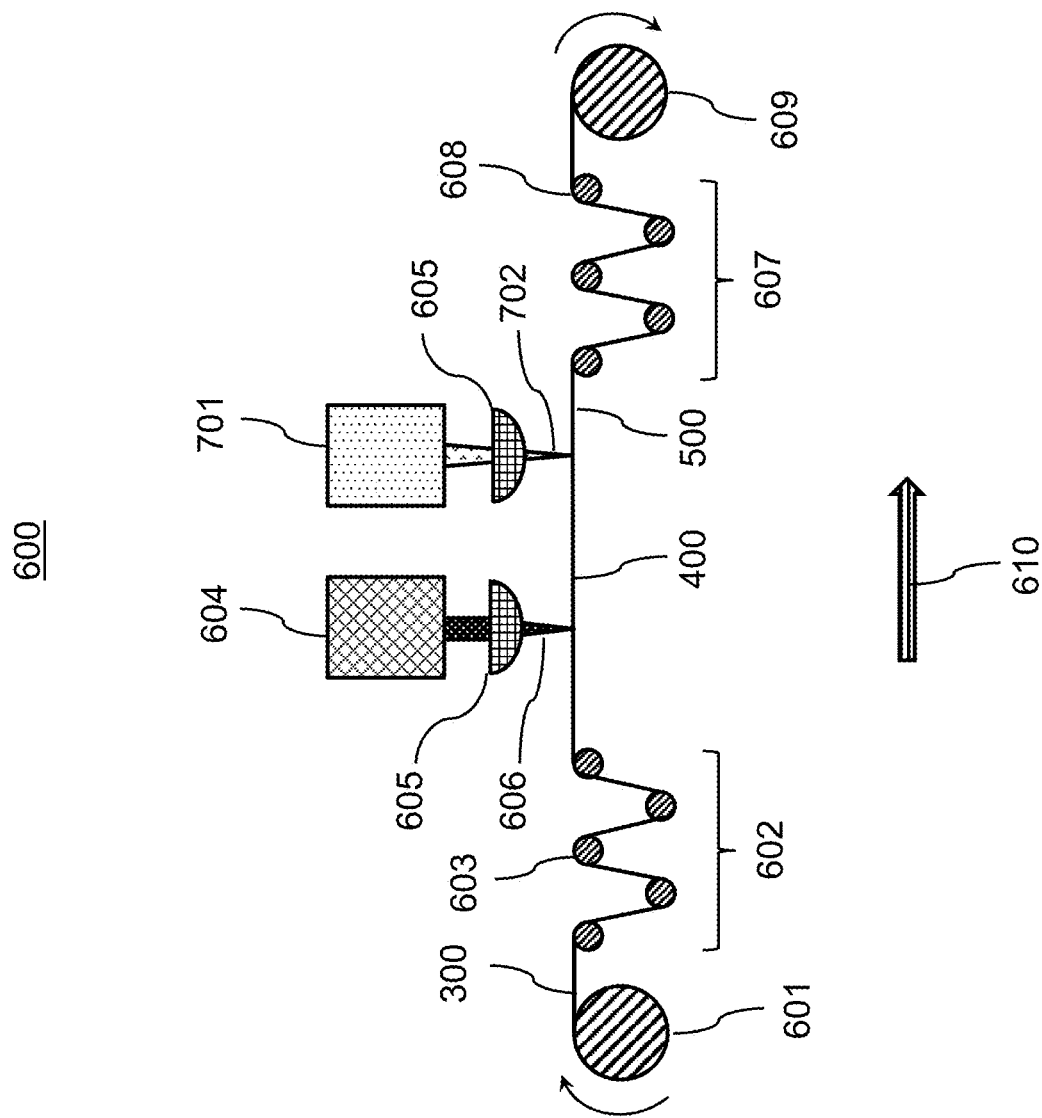
FIG. 7 a further device according to one embodiment.

FIG. 2 illustrates a flow-chart of a further process 100, according to one embodiment, for preparing a processed filament 500. Process steps a) 101 and b) 102 of this process 100 are identical to the process steps a) 101 and b) 102 of the process 100 of FIG. 1. In the process 100 of FIG. 2, a process step c) 201 follows. Therein, the segment of the processed filament 400 is further processed by interaction of the segment with a beam of electromagnetic radiation of a further kind 702 (see FIG. 7). The electromagnetic radiation of the further kind has a spectrum with a peak wavelength at 355 nm. The beam of electromagnetic radiation of the further kind 702 is a pulsed laser beam of a further kind. The laser beam of the further kind is pulsed at a frequency of 40 kHz, wherein each pulse has an energy of 3.20 and a duration of about 15 ns. For completely laser-ablating the first layer 302 of the processed filament 400 in the segment, the laser beam of the further kind is focused down to a focal beam diameter of 10 µm. Each pulse has a fluence of 4.1 J/cm$^2$. A cross-section through the processed filament 500, obtained in the process step c) 201, is illustrated in FIG. 5. A device 600 for carrying out the process 100 of FIG. 2 is illustrated in FIG. 7.

FIG. 3a) illustrates a cross-section through a filament 300. The cross-section has been made with perpendicular orientation to a length of the filament 300. Over its entire length of 3 km, the filament 300 consists inside-out of a core 301, which is made from platinum; a first layer 302, which is coated onto the core 301 and made from a polyurethane; and a second layer 303 which is coated onto the first layer 302 and consists of a mixture of silver and AgCl. The filament 300 has an overall diameter of 200 µm. A surface 304 of the first layer 302 has an average roughness R$_a$ of 0.7 µm and a root-mean-squared roughness R$_q$ of 2.5 µm. The surface 304 is an entire outer lateral surface of the first layer 302 which forms an interface between the first layer 302 and the second layer 303. The filament 300 is a wire. Here, the core 301, the first layer 302 and the second layer 303 are co-axial to one another. Accordingly, thicknesses of the first layer 302 and the second layer 303 are uniform over a circumference of the wire.

Figure 3B:
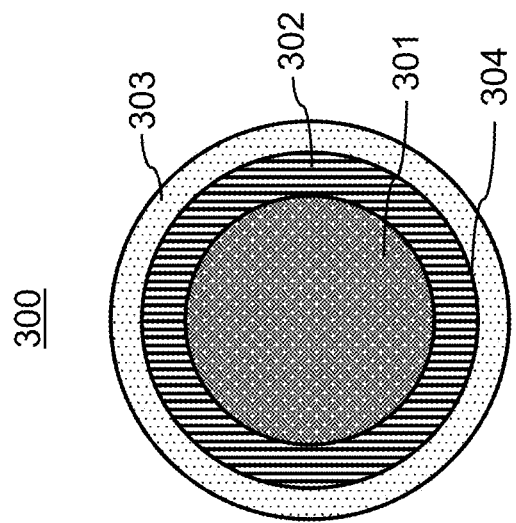
FIG. 3b) a cross-section through a further filament.

FIG. 3b) illustrates a cross-section through a further filament 300. The cross-section has been made with perpendicular orientation to a length of the filament 300. The structure of the filament 300 of FIG. 3b) is the same as that of the filament 300 of FIG. 3a). The filament 300 of FIG. 3b) is, as well, a wire. The wire of FIG. 3b), however, illustrates some eccentricity. Accordingly, a thickness of the second layer 303 is non-uniform over a circumference of the wire. This often occurs in practice with wires of the type illustrated in FIGS. 3a) and b). The eccentricity is illustrated in an exaggerated fashion in FIG. 3b).

FIG. 4 illustrates a cross-section through a processed filament 400. The processed filament 400 has been obtained in process step b) 102 of the process 100 of FIG. 1. The cross-section has been made through the segment of the processed filament 400 and with perpendicular orientation to a length of the processed filament 400. It can be seen that the second layer 303 has been completely ablated from circumferentially around the segment.

FIG. 5 illustrates a cross-section through a further processed filament 500. The processed filament 500 has been obtained in process step c) 201 of the process 100 of FIG. 2. The cross-section has been made through the segment of the processed filament 500 and with perpendicular orientation to a length of the processed filament 500. It can be seen that the first 302 and second layers 303 have been completely ablated from circumferentially around the segment.

FIG. 6 illustrates a device 600, according to one embodiment, for processing a filament 300 in a process stream 610, thereby obtaining a processed filament 400. The device 600 is configured for carrying out the process 100 of FIG. 1. Accordingly, the filament 300 is the same as described above in the context of FIG. 1. The device 600 includes a first source 604 which is designed and arranged for emitting the beam of electromagnetic radiation of the first kind 606 for laser-ablating the second layer 303 of the filament 300 in the segment from circumferentially around the segment, thereby obtaining the processed filament 400. The first source 604 is a Nd:YVO4-laser, the output of which is frequency-doubled in order to obtain the beam of electromagnetic radiation of the first kind 606 having the spectrum with the peak wavelength at 532 nm. The device 600 further includes a focusing means 605 which is a focusing objective. The device 600 is designed for a reel-to-reel-processing of the filament 300. Accordingly, the device includes a guiding means which, upstream of the laser, includes a filament feed that is designed to feed the filament 300 from a feed reel 601 which is also part of the device 600. Further, downstream of the laser, the guiding means includes a filament take-up means which is designed for the processed filament 400 to be rolled up on a take-up reel 609. Here, the guiding means includes the take-up reel 609. The guiding means further includes a first tension control means 6002 which is designed and arranged to adapt a tension of the segment of the filament 300 during the processing. The first tension control means 602 includes a first multitude of deflection rollers 603. In addition, the guiding means includes a further tension control means 607 which is arranged down-stream of the laser. The further tension control means 607, as well, is designed and arranged to adapt a tension of the segment of the filament 300 during the processing. The further tension control means 607 includes a further multitude of deflection rollers 608.

FIG. 7 illustrates a further device 600, according to one embodiment, for processing a filament 300 in a process stream 610, thereby obtaining a processed filament 500. The device 600 is configured for carrying out the process 100 of FIG. 2. Accordingly, the filament 300 is the same as described above in the context of FIG. 2. The device 600 of FIG. 2 is identical to the device 600 of FIG. 1, except for additionally including a further source 701 which is designed and arranged for emitting the beam of electromagnetic radiation of the further kind 702 for laser-ablating the first layer 302 of the processed filament 400 in the segment from circumferentially around the segment, thereby obtaining the processed filament 500. The further source 701 is also a Nd:YVO4-laser which is also equipped with a focusing means 605. Further, the output of further source 701 is frequency-tripled in order to obtain the beam of electromagnetic radiation of the further kind 702 having the spectrum with the peak wavelength at 355 nm.

Figure 8:
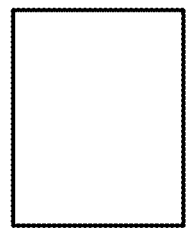
FIG. 8 an electrical device according to one embodiment.

FIG. 8 illustrates an electrical device 800 according to one embodiment. The electrical device 800 includes a 2 cm long part of the processed filament 400, obtained by the process 100 of FIG. 1, wherein the part includes the segment. Here, the electrical device 800 is a medical device and the part of the processed filament 109 is a component of an electrochemical sensor.

FIG. 9*a*) illustrates an illustration of parallel uni-directional processing. What is illustrated is a part of a filament 300, including a segment 901. Further, linear sweeps 902 (so-called lines) of a first multitude of linear sweeps (so-called pass) are depicted by arrows which illustrate a sweeping direction. Here, the linear sweeps 902 are conducted in the same direction. The linear sweeps 902 of the first multitude of linear sweeps are oriented in parallel to a length of the filament 300, as oriented in the segment 901. Further, a distance between the linear sweeps 902 (so-called pitch) is depicted.

FIG. 9*b*) illustrates an illustration of parallel bi-directional processing. What is illustrated is a part of a filament 300, including a segment 901. Further, linear sweeps 902 (so-called lines) of a first multitude of linear sweeps (so-called pass) are depicted by arrows which illustrate a sweeping direction. Here, a first fraction 904 of the linear sweeps 902 of the first multitude of linear sweeps is conducted in a first direction, wherein a further fraction 905 of the linear sweeps 902 of the first multitude of linear sweeps is conducted in a further direction, which is opposite to the first direction. The linear sweeps 902 of the first multitude of linear sweeps are oriented in parallel to a length of the filament 300, as oriented in the segment 901. Further, a distance between the linear sweeps 902 (so-called pitch) is depicted.

FIG. 9*c*) illustrates an illustration of perpendicular uni-directional processing. What is illustrated is a part of a filament 300, including a segment 901. Further, linear sweeps 902 (so-called lines) of a first multitude of linear sweeps (so-called pass) are depicted by arrows which illustrate a sweeping direction. Here, the linear sweeps 902 are conducted in the same direction. The linear sweeps 902 of the first multitude of linear sweeps are oriented perpendicular to a length of the filament 300, as oriented in the segment 901.

FIG. 9*d*) illustrates an illustration of perpendicular bi-directional processing. What is illustrated is a part of a filament 300, including a segment 901. Further, linear sweeps 902 (so-called lines) of a first multitude of linear sweeps (so-called pass) are depicted by arrows which illustrate a sweeping direction. Here, a first fraction 904 of the linear sweeps 902 of the first multitude of linear sweeps is conducted in a first direction, wherein a further fraction 905 of the linear sweeps 902 of the first multitude of linear sweeps is conducted in a further direction, which is opposite to the first direction. The linear sweeps 902 of the first multitude of linear sweeps are oriented in parallel to a length of the filament 300, as oriented in the segment 901.

Figure 10B:
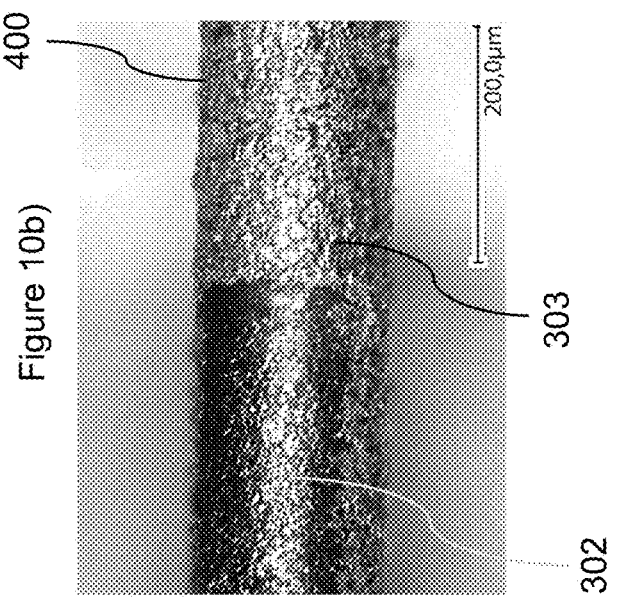
FIG. 10a) to optical microscope images of processed wires; and
c)
Figure 10A:
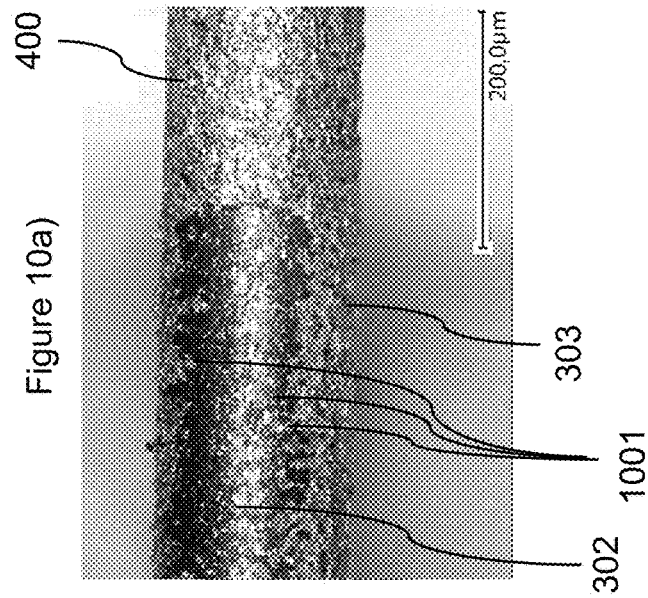
Figure 10C:
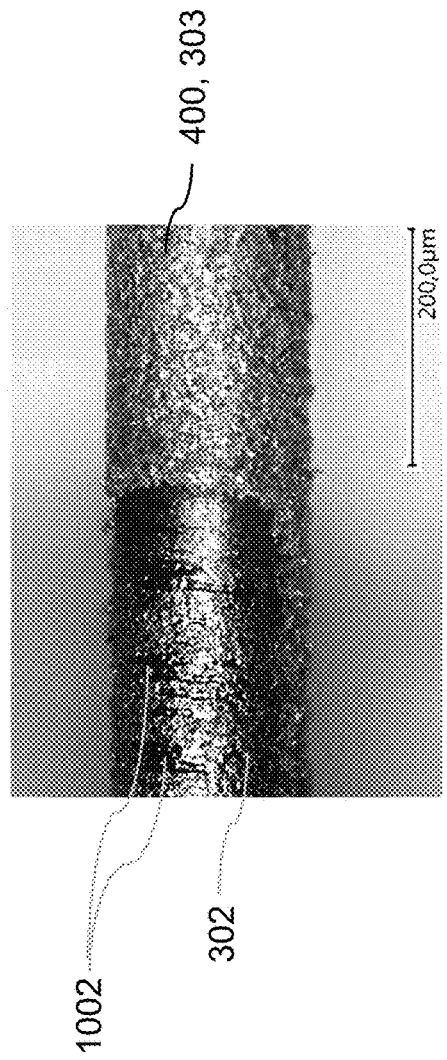

FIG. 10*a*) to c) illustrate optical microscope images of processed filaments 400 which are processed wires. These wires are of the structure illustrated in FIG. 3*a*), wherein processing of the wires has been conducted in order to completely remove the second layer 303 in a section of the circumference of a wire segment. In the case of FIG. 10*a*), residues 1001 of the second layer 303 remain on the first layer 302 in that section. This is inacceptable for manufacturing electrochemical sensors. In the case of FIG. 10 *c*), the second layer 303 has been removed completely from the section. However, the first layer 302, which is made of PU, has been molten in regions 1002. Only in the case of FIG. 10*b*), the second layer 303 has been laser-ablated completely from the section of the segment, essentially without damaging the first layer 302 underneath.

Figure 11:
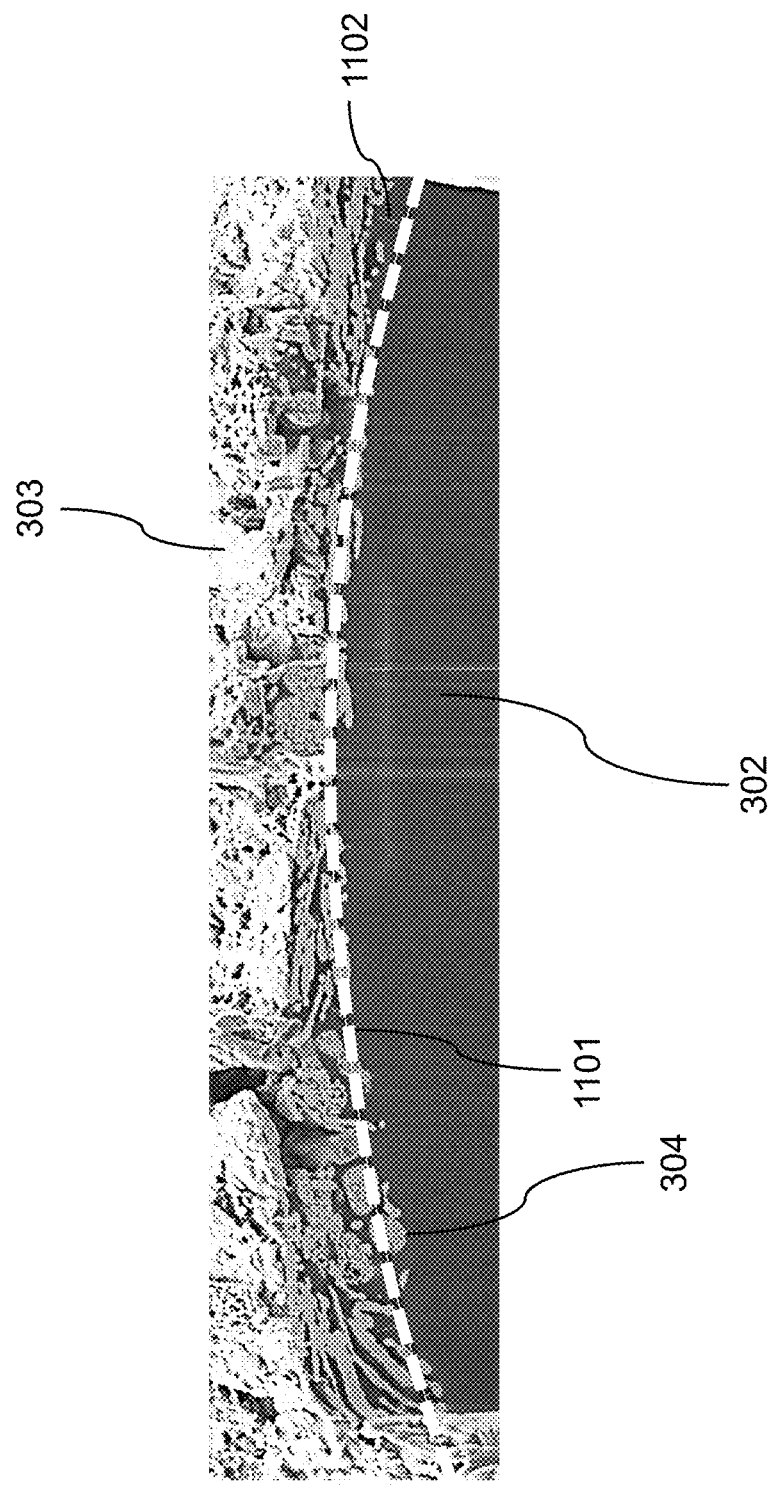
FIG. 11 a focused-ion-beam image of a cross-section of a wire for determining a roughness of a surface of a first layer of the wire.

FIG. 11 illustrates a focused-ion-beam image of a cross-section of a wire for determining a roughness of a surface of a first layer of the wire. What can be seen is an interface between a first layer 302, which is a PU-layer, and a second layer 303, which is an Ag/AgCl-layer. This interface is at an outer lateral surface 304 of the first layer 302. A circle 1101 has been drawn into the image as described above in the test methods section. Further, a distance 1102 between the circle 1101 and the surface 304 is depicted at equidistant positions along the circle 1101.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A process for preparing a processed filament, the process comprising:
   a) providing a filament, comprising a segment,
      wherein, at least in the segment, the filament comprises
      i) a core, comprising a first metal,
      ii) a first layer which
         I) is superimposed on the core, and
         II) comprises a polymer, and
      iii) a second layer which
         I) is superimposed on the first layer, and
         II) comprises a second metal; and
   b) processing the segment of the filament by interaction of the segment with at least one beam of electromagnetic radiation of a first kind;
   wherein the electromagnetic radiation of the first kind has a spectrum with a peak wavelength in the range from 430 to 780 nm, and
   wherein a surface of the first layer has an average roughness $R_a$ in the range from 0.07 to 4 µm.

2. The process of claim 1, wherein a surface of the first layer has a root-mean-squared roughness $R_q$ in the range from 0.2 to 7 µm.

3. The process of claim 1, wherein the at least one beam of electromagnetic radiation of the first kind is at least one laser beam of a first kind, wherein the at least one laser beam of the first kind is at least one pulsed laser beam of the first kind.

4. The process of claim 3, wherein the at least one pulsed laser beam of the first kind is characterised by a pulse duration in a range from 10 fs to 500 ns.

5. The process of claim 3, wherein a fluence of the at least one pulsed laser beam of the first kind is in the range from 1.0 to 5.0 J/cm$^2$ per pulse.

6. The process of claim 3, wherein the at least one pulsed laser beam of the first kind is characterised by an energy per pulse in the range from 2 to 15 µJ.

7. The process of claim 1, wherein, in the step b), the processing comprises at least partially removing the second layer from the segment of the filament.

8. The process of claim 1, wherein the process further comprises:
 c) further processing the segment of the filament by interaction of the segment with at least one beam of electromagnetic radiation of a further kind.

9. The process of claim 8, wherein the electromagnetic radiation of the further kind has a spectrum with a peak wavelength in the range from 10 to 430 nm.

10. The process of claim 8, wherein, in the step c), the further processing comprises at least partially removing the first layer from the segment of the filament.

11. The process of claim 1, wherein the filament is one selected from a group consisting of a wire, a cable, and a fibre, or a combination of at least two thereof.

12. The process of claim 1, wherein a surface of the first layer has an average roughness $R_a$ in the range from 0.2 to 4 µm.

13. The process of claim 1, wherein the surface of the first layer faces the second layer.

* * * * *